(12) United States Patent
Steck et al.

(10) Patent No.: US 10,850,032 B2
(45) Date of Patent: Dec. 1, 2020

(54) DEVICE FOR ADMINISTERING A FLUID PRODUCT

(71) Applicant: Ypsomed AG, Burgdorf (CH)

(72) Inventors: Jürg Steck, Kirchberg (CH); Jan Baumert, Grunen (CH); Christoph Lauster, Liebefeld (CH); Thomas Gurtner, Koppigen (CH); Réne Mathys, Aarau (CH); Patrick Hostettler, Hasle (CH); Nicolas Binggeli, Burgdorf (CH); Thomas Buri, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 766 days.

(21) Appl. No.: 15/246,868

(22) Filed: Aug. 25, 2016

(65) Prior Publication Data

US 2016/0361494 A1 Dec. 15, 2016

Related U.S. Application Data

(63) Continuation of application No. PCT/EP2014/053668, filed on Feb. 26, 2014.

(51) Int. Cl.
*A61M 5/172* (2006.01)
*A61M 5/142* (2006.01)
*A61M 5/168* (2006.01)

(52) U.S. Cl.
CPC ........ *A61M 5/172* (2013.01); *A61M 5/14216* (2013.01); *A61M 5/14244* (2013.01);
(Continued)

(58) Field of Classification Search
CPC .............. A61M 5/14244; A61M 5/145; A61M 5/1452; A61M 5/1456; A61M 5/14566;
(Continued)

(56) References Cited

U.S. PATENT DOCUMENTS 5,993,423 A 11/1999 Choi
6,248,093 B1 6/2001 Moberg
(Continued)

FOREIGN PATENT DOCUMENTS

EP 0 985 419 A1 3/2000
EP 1 426 662 A1 6/2004
(Continued)

OTHER PUBLICATIONS

Vimalavathini et al., Indian J. Med. Res. 130, Aug. 2009, pp. 166-169.
(Continued)

*Primary Examiner* — Bhisma Mehta
*Assistant Examiner* — Larry R. Wilson
(74) *Attorney, Agent, or Firm* — Dorsey & Whitney LLP

(57) ABSTRACT

An infusion apparatus for delivering medication includes a housing, a drive mechanism, a force sensor, and a transfer element. The drive mechanism comprises first and second conveying elements, the second conveying element for advancing a plug in a reservoir in the distal direction, the first conveying element with limited axial movement relative to the housing but rotatable to cause an ejecting or resetting movement of the second conveying element. The force sensor is arranged along a central axis between the housing and the proximal end of the drive mechanism. The transfer element is axially arranged between the force sensor and the first conveying element and the force sensor bears axial forces exerted by the ejection movement. The second conveying element moves the transfer element away from the first conveying element against the bias of a restoring force such that the force sensor bears axial forces exerted by the resetting movement.

20 Claims, 16 Drawing Sheets

(52) U.S. Cl.
CPC ............... *A61M 5/16831* (2013.01); *A61M 2005/16863* (2013.01); *A61M 2205/18* (2013.01); *A61M 2205/332* (2013.01); *A61M 2205/3331* (2013.01); *A61M 2205/3368* (2013.01); *A61M 2205/502* (2013.01); *A61M 2205/52* (2013.01); *A61M 2205/702* (2013.01); *A61M 2205/8206* (2013.01)

(58) Field of Classification Search
CPC .. A61M 5/168; A61M 5/16831; A61M 5/172; A61M 2005/14506; A61M 2005/14573; A61M 2205/332
See application file for complete search history.

(56) References Cited

U.S. PATENT DOCUMENTS

| | | | | |
|---|---|---|---|---|
| 6,368,314 | B1* | 4/2002 | Kipfer | A61M 5/14546 222/309 |
| 7,597,682 | B2 | 10/2009 | Moberg | |
| 8,495,918 | B2* | 7/2013 | Bazargan | A61M 5/14248 73/818 |
| 2002/0171297 | A1 | 11/2002 | Talbot | |
| 2005/0197626 | A1 | 9/2005 | Moberg et al. | |
| 2008/0125700 | A1 | 5/2008 | Moberg et al. | |
| 2008/0269673 | A1 | 10/2008 | Butoi et al. | |
| 2012/0165780 | A1* | 6/2012 | Bazargan | A61M 5/14244 604/500 |
| 2013/0076518 | A1 | 3/2013 | O'Connor | |
| 2015/0080842 | A1 | 3/2015 | Mathys | |

FOREIGN PATENT DOCUMENTS

| | | |
|---|---|---|
| EP | 2 052 752 B1 | 11/2011 |
| WO | WO 2004/024217 | 3/2004 |
| WO | WO 2004/091688 A2 | 10/2004 |
| WO | WO 2005/018721 | 3/2005 |
| WO | WO 2006/061170 | 6/2006 |
| WO | WO 2009/035759 | 3/2009 |
| WO | WO 2010/026580 | 3/2010 |
| WO | WO 2011/022850 A2 | 3/2011 |
| WO | WO 2011/080092 | 7/2011 |
| WO | WO 2012/054236 | 4/2012 |

OTHER PUBLICATIONS

Correira M. et al., UV-light exposure of insulin: Pharmaceutical Implications upon covalent insulin dityrose dimerization and disulphide bond photolysis, PLOS One, vol. 7 (12), 2012.
International Preliminary Report on Patentability dated Aug. 30, 2016, for International Application No. PCT/EP2014/053668 filed on Feb. 26, 2014.
International Search Report dated Jul. 1, 2014, for for International Application No. PCT/EP2014/053668 filed on Feb. 26, 2014.

\* cited by examiner

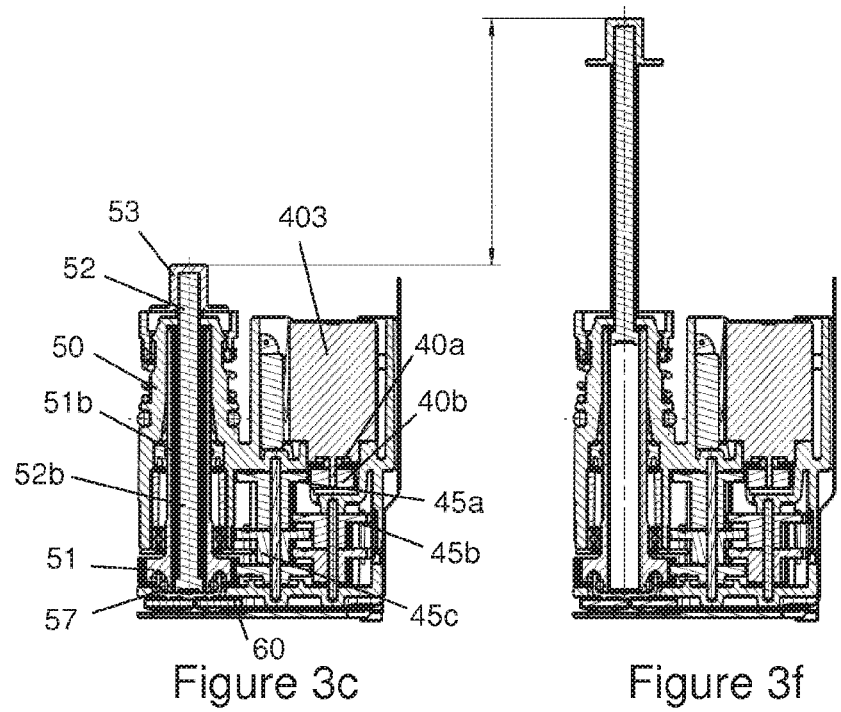
Figure 3c
Figure 3f
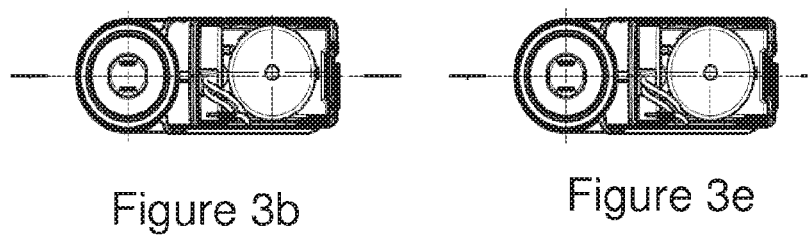
Figure 3b
Figure 3e
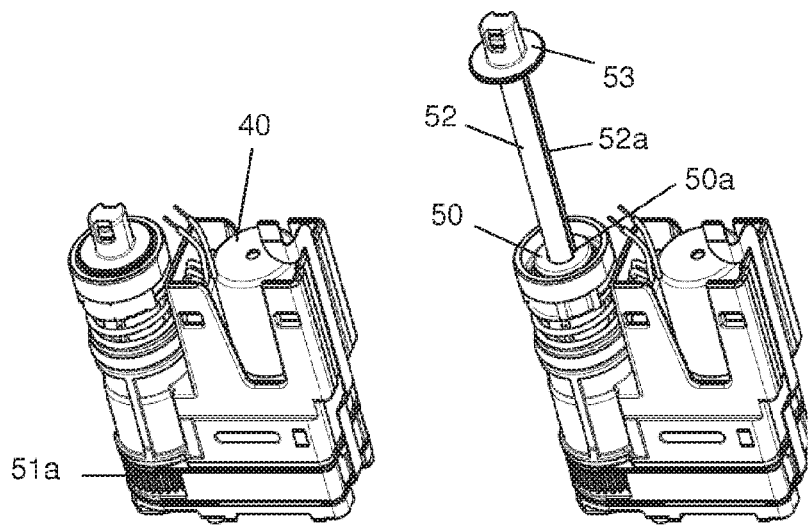
Figure 3a
Figure 3d

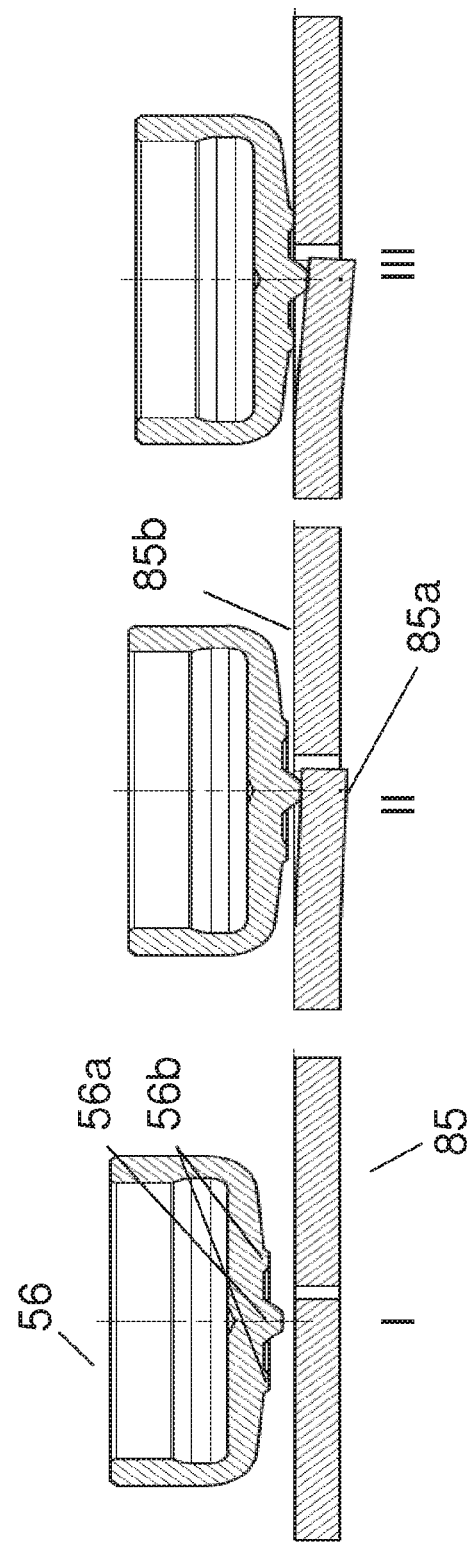

DEVICE FOR ADMINISTERING A FLUID PRODUCT

CROSS-REFERENCE TO RELATED APPLICATIONS

This application is a Continuation of International Patent Application No. PCT/EP2014/053668 filed Feb. 26, 2014, the entire contents of which are incorporated herein by reference for any and all purposes.

BACKGROUND

The present invention relates to a device or portable administering apparatus for administering a fluid product, in particular medical substances or a drug in liquid form. In particular the invention relates to a portable infusion pump and/or infusion systems such as insulin pumps. Such a device is referred to in the following as an administering device. In the case of various diseases, it can be necessary to administer a patient over a longer period of time with a drug which is provided in liquid form, for example an insulin preparation or a haemodiluting drug such as heparin. Compact portable infusion apparatuses are known for this purpose, which are continuously carried around close to the body by the patient. In most cases, a carpoule is provided as the drug container in such infusion apparatus, i.e., a plastic or glass container comprising a plug which can be moved within it. The carpoule (often also referred to as an ampoule or reservoir) is connected to an infusion set, the cannula of which feeds into the body tissue of the patient. The plug or stopper is advanced in the carpoule by a suitable drive, for example a spring drive or an electric motor, and the drug is thus expelled from the carpoule. As soon as the carpoule is empty, it is removed from the infusion apparatus and replaced with a new carpoule.

In many portable infusion apparatuses, the plug is advanced in the carpoule via a threaded rod, which acts as a piston rod for the plug. A nut which is mounted such that it is rotatable but fixed against shifting, runs on the threaded rod and is driven by an electric motor. Rotating the nut advances the threaded rod, wherein the electric motor is in generally arranged next to the carpoule in order to limit the length of the infusion apparatus and to simplify exchanging the carpoule.

U.S. Pat. No. 6,248,093 B1 discloses an infusion apparatus in which the drive motor and a gear system are arranged coaxially with the drug reservoir. The plug of the drug reservoir is advanced by a sleeve-like advancing element which is connected via an inner thread to a drive screw, which is driven by the motor, and thus linearly advanced. In its initial position, the advancing element at least partially surrounds the gear system of the motor, wherein the advancing element is a part of the base unit, while the plug is part of the exchangeable drug reservoir. The advancing element and the plug are therefore embodied such that they can be separated from each other. In order to ensure that the drug is not undesirably expelled by fluctuations in the ambient pressure, the advancing element and the plug are connected such that the connection can also absorb tensile forces while the infusion apparatus is in operation. In this way, the plug necessarily follows the movement of the advancing element and cannot be advanced, by pressure fluctuations, further than is predetermined by the position of the advancing element. When the drug reservoir is exchanged, the plug and the advancing element are separated from each other by a rotational movement. The advancing element is then moved back into its initial position by the motor. On the one hand, this arrangement requires a relatively complicated connection between the plug and the advancing element; particular steps also have to be taken in case a drug reservoir which is not completely filled is used.

An infusion apparatus is known from EP 0 985 419 A1 in which the drive motor and a drug reservoir are arranged antiparallel with respect to each other, wherein a gear system transmits the drive movement from the motor to an advancing element which is arranged coaxially with respect to the reservoir and in turn moves the plug provided in the drug reservoir, thus displacing the drug from the reservoir. A so-called infusion set adapter is attached to the exit of the drug reservoir and channels the drug into an infusion set. In order to ensure that the drug is not undesirably expelled by fluctuations in the ambient pressure, a threshold value valve is arranged in the infusion set adapter and requires a particular drive pressure in order to enable liquid to be transported through the infusion set adapter at all. As compared to the variant described above, in which the plug is retained by the advancing element, the threshold value has the advantage that standard carpoules for the infusion apparatus can be used; in particular, specially shaped plugs are not required. It is however known that when the threshold value valve is a membrane valve, an inaccurate positioning of the valve membrane can potentially lead to malfunctions and in particular valve leakage, and that accurately positioning the membrane presents a production-related challenge. U.S. Pat. No. 5,993,423 describes a portable automatic syringe device and an injection needle unit thereof.

U.S. Pat. No. 7,597,682 B2 describes an external infusion device for infusion of a fluid into a body from a reservoir including a drive system, a housing, an electronic control circuitry and at least one vent port. The vent port in the housing permits the passage of air into and out of the housing and inhibits the passage of liquids into the housing.

A sensor assembly for measuring axial loads (forces) in medical devices is described in U.S. Pat. No. 8,495,918 B2. The sensor encompasses a central part mechanically connected to an outer ring structure via a number of connecting units. Upon loading, the central part is axially displaced versus the outer ring and this axial displacement results in a deformation of the connecting units which is measured by thin film sensors present on the surface of the connecting units. The deformation and resistance of the thin film sensors on the connecting units is measured and the electrical signal is transformed into a load signal (forces). The maximum axial displacement of the central unit is restricted by a separate back plate present behind the sensor to prevent excessive elastic deformation of the connecting unit coated with the thin film sensors. In EP 2 052 752 B1, an infusion device for the administration of a medication is described with an occlusion recognition system based axial force measurements by a force sensor unit. The medication is expelled from the carpoule by a piston rod driven by a drive mechanism that is based on a free floating element. The reactive forces for the advancement of the piston rod are transmitted to the free floating element that is pressing against a cantilever beam of the force sensor unit. Upon reset of the device, the free floating element is brought back into its original position by the resilient forces of the cantilever beam of the force sensor unit. The cantilever beam compensates for the gravitational and frictional forces acting on the free floating element and as a consequence the cantilever beam is pre-stressed to compensate for these forces for a correct adjustment of the zero force position.

A user of an administering device may travel through various elevations, which might occur when hiking in the mountains or travelling in an airplane, so that differential pressures can arise between the interior of the air tight or water-resistant pump housing and the outside or atmosphere. Once the pressure in the housing exceeds the external atmospheric pressure, resulting forces could cause the reservoir plug or reservoir piston to be driven inwards and thus delivering unwanted medication. Problems with the correct functioning of the administering device may also occur in case the outside atmospheric pressure exceeds the inside pressure of the housing. It is desirable to have an administering device which guarantees safe operation among various atmospheric pressures.

SUMMARY

It is an object of an embodiment of the present invention to provide an administering device or infusion device with an improved force measurement means and methods for improved force measurement.

In an embodiment of the present invention the administering device has a drive system with an improved reset functionality. The administering device delivers medication from a reservoir with a plug moveable along a central axis. During delivery, the plug is advanced along the central axis in the distal direction by a piston rod. During reset, the piston rod is retracted back along the same axis in the proximal direction into the device and finally touches and axially displaces a transfer element. The transfer element transmits the axial force from the retracting piston rod to a force sensor but also protects the force sensor from overloading as is described herein. The force sensor comprises a base plate and a cantilever beam connected to the base plate. Deflection of the cantilever beam versus the base plate also deforms a layer or coating present on the cantilever beam and this deformation is transformed into a measurable force signal. The piston rod is retracted until a certain force level is reached which may be below the maximum measurement range of the sensor. An advantage of the present invention is that the force sensor does not need a separate back plate structure or otherwise supporting structure for preventing overloading of the sensor because the overload protection is integrated in the transfer element. The transfer element comprises a force transmitting element for transmitting the axial forces from the drive train to the deflecting beam of the sensor, and a restricting element which can interact with the base plate of the sensor restricting the maximum deflection of the beam and therewith the upper limit of the force measurement range. Additionally, the improved reset functionality ensures that the transfer element automatically returns and is axially relocated to the original position before the transfer element was touched by the retracting piston rod. During reset, the transfer element is axially displaced by the rewinding piston rod against a biasing or restoring force which wants to bring back the transfer element to the original position. This force can be exerted by a resilient member such as an elastomeric material (e.g. an O-ring, a gel) or an extension or compression spring. The restoring force can also be exerted by other means such as a magnetic or electromagnetic force. The return of the transfer element to the original position ensures that there is no contact, or minimal contact, or no load-bearing contact between the force sensor and the transfer element after reset of the device. This is advantageous for accurate calibration of the force sensor since it is unloaded after resetting the device but before insertion of a new reservoir with medication. Therewith the force sensor is not loaded by the transfer element, e.g., the sensor is completely unloaded to ensure accurate calibration, particularly a zero force calibration of the force sensor after each reset operation.

As an alternative, and a reversal of the above-described situation, the force transmitting and restricting elements are part of the force sensor and interact with a transfer element having a planar surface. Although being an alternative, this option is less favourable for accurate reset of the device and calibration of the force sensor.

These objects are solved by an infusion apparatus of claim 1 or by a device for administering a fluid product, comprising an infusion set and an administering apparatus. Preferred embodiments and methods are specified in the dependent claims.

It is a further aspect to provide a device for administering a fluid product using an electrically driven motor, the device having an improved energy management system for the power supply. The energy management system may comprise a second battery source and an electronic circuit that enables both fast and normal loading of the second battery source. An example of the electronic circuitry is described in WO 2011/022850 which is included here for reference. A battery recognition system may be included in the device to identify the type of battery or rechargeable battery inserted into the device. This has the advantage that the energy management of the infusion apparatus is adapted to the specific discharge profiles for each type of battery. For example the alarm for exchanging an empty battery may be adapted to the specific type of battery used. The battery compartment may be made from a non-conductive material or a conductive material. The non-conductive material is an electrically insulating plastic whereas the conductive material is a metal or a coated metal or a polymer coated with an electrically conductive layer or an electrically conductive material embedded in a plastic material. The battery compartment is closed by a lid forming one of the terminals for the electronic circuitry contacting the battery. The electronic lid may have an integrated reverse battery protection and can be made from an electrically insulating material or from an electrically conductive material or from an electrically insulating material coated with an electrically conductive material or from a combination thereof. A battery lid constructed from a metal has the advantage that wear, through repeated insertion and release, is reduced and therewith the longevity of the lid is extended. An electrically conductive battery compartment may have the advantage that it is part of the electronic circuitry providing the connection to the minus and plus terminal of the battery and it may have additional functions such as an antenna or a receiver for wireless communication and/or electromagnetic or electrostatic shielding purposes. The battery compartment itself may form a waterproof barrier versus the ambient, both the positive and the negative terminal may be sealed using appropriate O-rings.

In further examples, the functioning of the device is monitored using other sensors that can measure temperature, humidity, mechanical impact or pressure, this to ensure that the housing of the device is intact and to protect the drive mechanism and control unit from environmental influences.

The medical device as described before is subjected to environmental influences such as high or low temperature, sunlight, mechanical impact due to dropping of the infusion apparatus leading to damage of the housing or high humidity. It is an aspect to improve the infusion apparatus and reduce or eliminate these influences on the performance of the device.

The medication administered by the device is subjected to thermal degradation or a loss of effectiveness due to the exposure to sunlight and/or increased temperatures. Such exposure to elevated temperatures far above 40° C. is, for example, likely to happen if the device is in the trunk of a car exposed to sunlight where temperatures exceeding 40° C. are feasible. Protein structures such as insulin denature due to changes in the 3-dimensional structure and this reduces its therapeutic effect. It was shown by Vimalavathini et al., Indian J. Med. Res. 130, 166-169, that the potency of commercially available insulin reduces by 18% if exposed for 28 days at 37° C. On the other hand low temperature freezes the medication, again leading to a reduced effectiveness. For example exposure of insulin to temperatures below 0° C. leads to clumping and aggregation of the proteins. Not only is the medication influenced by thermal stresses but also the hardware components present in the device such as the electromotor, the gearing wheels, the power supply unit such as the battery package, the control unit or the display. Increased temperature of the plastic components leads to thermal expansion resulting in misalignments or malfunctioning of the device. In WO04024217, problems with the dose accuracy at elevated temperatures for delivering insulin using an infusion device are described. On the other hand a lower temperature potentially leads to embrittlement of the plastic components reducing the functionality of the device and/or the device is more vulnerable to impact damage. Therefore a sensor can be included in the device that measures the temperature of the device, and this can be the temperature inside the device or the outside surface temperature of the device. The sensor measures the temperature and the signal is sent to an electronic control module. The measured temperature value is compared with a defined alarm value or alarm function sequence, or a defined sequence of values and the electronic module triggers an alarm if the temperature exceeds this alarm value. The measured temperature may be integrated over time to simulate or predict the status of the active ingredients or the device parts. The alarm is a tactile, audible or visual signal that is easily notified by the user of the device. Optionally, the alarm is sent by wireless communication to another device such as a remote control for the infusion pump or a blood glucose measuring unit or to a cellular phone or a personal computer, or a software implemented application or a health care professional or any other network device. The alarm is logged in a history file of the infusion device or any of the devices receiving the signal from the infusion device.

The infusion devices are daily used by a patient and worn close to the body during activities such as sports, showering or walking. A high humidity inside the infusion device could be an indication that there is a void or crack in the housing of the device as a result from mechanical impact, misaligned parts or improper insertion of the carpoule, infusion set or battery compartment lid. The increased humidity can lead to fluid condensation on electronic components of the control unit which might lead to corrosion or electronic short cuts and harm the proper functioning of the device. The electronic components need to be properly shielded from these environmental influences as is described in US 2002/0171297 and/or the user is notified that there is an increased humidity inside the device. Therefore a humidity sensor can be part of the current infusion apparatus, the sensor measures the humidity level, i.e., the relative humidity and/or the presence of condensed water, and the control unit compares the measured value with an alarm level and triggers the alarm if the humidity exceeds the alarm level. The alarm triggered is a tactile, audible and/or visual alarm and is notified to the user by the device itself or sent to a receiver as described above for the temperature sensor system.

An infusion apparatus is normally waterproof sealed to prevent humidity entering the housing which could lead to damage to the electronic components of the system as described above. The first barrier for liquids to enter the infusion apparatus is formed by the external housing. Damage to the housing, for example due to mechanical impact can lead to (micro) cracks or voids in the housing part and thus create a path for fluids to enter into the infusion device. One option to warn the user of such a device is by implementation of the humidity sensor described before. Another option for providing a means to detect the integrity of the housing is by measuring the pressure inside the housing. In US 2013/0076518, a pressure sensor measures the difference between the pressure outside and inside the device. The object of that invention is to measure pressure changes between the outside and inside of the device depending on whether the user is at a different altitude or travels by airplane. Here, in one example the pressure inside the device is measured and variations of the inside pressure over time are detected, particularly for a housing that is air-tight. Any deviation from a normal pressure pattern for an intact housing is an indication that the infusion device is no longer airtight. Those pressure variations inside the housing are the result of volume changes in the housing or sealed compartments within the housing due to moving parts such as the piston rod. Depending on the remaining volume of the injectable liquid in the carpoule, the corresponding position of the piston rod will lead to a different volume inside the housing or compartments within the housing. After resetting the device, the piston rod is retracted in its utmost proximal position and a new carpoule is inserted whereas the piston rod is driven distally during repeated dose deliveries until the carpoule is empty. The volume changes inside the housing lead to pressure fluctuations in the housing. If the carpoule is full, the pressure is higher (volume inside the housing is lower) compared to the situation when the carpoule is empty (volume inside the housing has increased). During reset, the piston rod is moved in a proximal direction decreasing the volume in the housing resulting in an increased pressure. During repeated emptying of carpoules and resetting of the device, a normal pressure fluctuation profile is measured by a pressure sensor located inside the housing and this standard pressure profile is also stored in a memory. If there is any damage to the housing or the sealing rings used in the housing, a deviation from this pressure profile is observed since there is air leakage through the cracks or voids of the housing. The measured pressure profile deviates from the standard pressure profile and the processor alerts an audible, tactile or visual alarm to the user. The pressure normally increases during reset of the piston rod in an intact housing and any deviations are signaled to the user prior to the insertion of a new carpoule, thereby notifying the user before using the infusion apparatus. Such a change of the carpoule is done at intervals varying between 1 and 5 days and thus the user gets a regular feedback that the integrity of the housing is guaranteed. As mentioned before, this working principle is applicable to a housing that is air tight such that small differences of the inside volume lead to pressure differences that are measured by an internal pressure sensor. Another option for this pressure sensing system is to use it in combination with a housing having an air permeable connection to the outside. A pressure equalization device is beneficial for the infusion apparatus since it prevents pressure built up in the device due to a decreasing ambient pressure resulting from an increased altitude (mountains) or a reduced aircraft cabin pressure. The increased pressure inside the device can lead to unwanted delivery of medication which should be prevented. Such an air permeable connection is achieved by a suitable semi-permeable membrane as is described herein that is part of the housing of the infusion device. The volume changes due to a moving piston rod will not lead to pressure fluctuations inside the housing since there is an air permeable connection to the outside of the housing. However, where such a membrane is blocked, dirty or contaminated, then the inside volume changes will lead to a specific pressure profile and this profile can be measured by a pressure sensor located inside the housing. During reset and emptying of a carpoule, a pressure profile is recorded resulting from the moving piston rod which, in contrast to the application above, is undesirable since it is related to hermetic closure of a device that intentionally has an air permeable membrane located in the housing. The pressure profile recorded for a clogged membrane triggers an alarm and this alarm is transmitted to the user by audible, tactile and/or visual means.

The integrity and functionality of the infusion apparatus after a mechanical impact can be monitored by integration of an acceleration sensor in the apparatus. An acceleration sensor is described in US 2008/0125700 for measuring the activity level of the patient wearing the infusion apparatus and providing inputs for a feedback loop to the internal control unit for adjusting the amount of medication depending on the physical activity level of the patient. In the present device, accelerations beyond the normal activity level can be measured, for example a drop of the infusion device on the floor. This could damage the housing or mechanical or electronic components inside the infusion apparatus. During such an impact, the sensor sends a signal to the control unit and the control unit logs this signal and triggers an alarm if the signal is above a safety limit indicating by means of visual, audible and/or tactile means an impact to the user of the device. A message is communicated to the user indicating that he or she should check the apparatus and/or send the infusion device to the manufacturer for a control check. In a further example, a device for administering a fluid product is presented, comprising an infusion set and an administering apparatus, which offers increased reliability and improved safety and which can be operated with standard-dimension carpoules.

Such a device comprises an actual administering apparatus, in particular, an infusion pump and an infusion set which establishes a liquid connection between the administering apparatus and an injection needle, wherein the administering needle is injected into the tissue of the person using the device, in order to administer a fluid product, for example a liquid drug.

The design of the administering apparatus corresponds essentially to the commercially available mobile infusion pumps for insulin which are known to the person skilled in this art, such as those currently sold by manufacturers such as Roche or Medtronic, wherein the administering apparatus comprises at least the following components: a housing; a container for the product, which is at least partially accommodated by the housing; a conveying means for conveying the product from the container; and a drive device. The infusion set comprises at least one single-part or multi-part adapter which establishes a liquid connection between the product container and the infusion set and which can be detachably fastened to the administering apparatus.

The drive system of the device preferably comprises a drive motor and a controller. In a preferred example, the drive system also comprises a spindle drive which acts on the conveying means. In another example, a gear system is arranged between the drive motor and the spindle drive and gears up or gears down the movement of the motor. In one example, the container filled with product can be a pre-filled ampoule, in particular a so-called carpoule. Alternatively, the container can also be a reservoir which is to be filled by the person using the device. The container can be an ampoule or a container made from a flexible material, or a collapsible container or a pouch type of container. Common to all the examples of the containers is that they can be inserted into a receiving compartment, formed by the housing, and exchanged. The product is preferably a medical and/or cosmetic active agent solution, emulsion or suspension. The conveying means is preferably a stopper, a piston or a plug. The device is preferably worn continuously by the person using it, either on their body or on or in their clothing.

In one example, the administering apparatus comprises at least one means for determining a malfunction of the device. This malfunction can be due to an occlusion or a leakage on the product's path from the container to an outlet of the injection needle. Another example of a malfunction can be due to the drive device, for example a faulty or disrupted drive motor or a faulty controller and/or regulator for a drive motor. In one example, the administering apparatus comprises an input means and a display means, wherein the input means and display means can be at least partially combined in an advantageous example, in particular as a touch display, wherein the combination of a touch display and an individual key which is distinct from the touch display has proven preferable. Other input means can be provided, such as for example a speech input. In principle, the input means and display means enable the person using the device to personally influence how product is administered. In one advantageous improvement, the key is arranged in the housing of the administering apparatus, forming a seal, such that water cannot enter the interior of the administering apparatus or the interior of the key. In one example, the adapter of the infusion set comprises a housing, wherein an open cylinder is arranged on one side of the housing and can be introduced into an opening of the receiving compartment of the administering apparatus. For the purpose of fastening the cylinder in the receiving compartment, elements are arranged on the outer surface of the cylinder shell and can be engaged with matching counter-elements on the inner surface of the receiving compartment, wherein they can be engaged by inserting the cylinder along the longitudinal axis of the receiving compartment or alternatively via a screw connection or a bayonet lock. In the interior of the cylinder, a so-called connecting needle is arranged coaxially with respect to the axis of the cylinder. When an adapter is inserted into the administering apparatus, the connecting needle pierces a wall of the product container, in particular a septum, and establishes a liquid connection between the container and the infusion set, wherein the needle is preferably formed so as to be hollow. It is an object to prevent piercing of the septum by the needle outside the center of the septum and to prevent other misaligned piercing such as off-axis (non-transversal) or cork screw type of piercing. Therefore the elements on the outer surface of the adapter cylinder and the inner surface of the receiving compartment are arranged such that the connecting needle is axially guided and pierces the septum of the container at the correct angle and location in the center of the septum. An opening is arranged on another side of the adapter housing, and the catheter of the infusion set can be detachably or non-detachably arranged in said opening, wherein a liquid path is arranged in the housing such that a liquid connection between the connecting needle and the catheter is established. In one advantageous example, a valve is arranged in the liquid path of the housing. This valve is intended to prevent any undesirable leakage from the product container, to such an extent that the person using the device cannot receive any incorrect dosage which would be hazardous to them. This is important in particular when there is a difference in pressure between the administering apparatus and the injection needle. The administering apparatus can for example be arranged higher than the injection needle. The force and/or pressure of the column of liquid which is then present can thus cause the product container to be emptied if there is not a sufficiently large resistance or counter-pressure inside the product container. Since the quality of typical product containers such as for example carpoules is subject to fluctuations in production, and the piston or plug which is arranged such that it can be shifted in the carpoule exhibits a fluctuating plug friction against the carpoule wall, a means which enables product to be administered only once a minimum drive force is exerted by the drive device is eminently important. The valve arranged in the adapter is essentially closed when the administering apparatus is in its resting state. Only once the drive device is activated and a sufficiently high and defined pressure is acting on the valve, does the valve open and enable larger amounts of product to flow through it. In one example, the valve can be a membrane valve, wherein it is important for the valve membrane to be positioned, centered, on the valve seating. Only when the valve is cleanly centered is it possible to ensure that the valve only opens at a defined pressure. If the centering is off, then the periphery of the valve membrane may touch an inner wall of the valve. Consequently, the periphery of the valve membrane will rub against the wall of the valve. When the drive device is activated, this can cause the membrane for opening the valve to open due to the operation-related pressure, i.e., to move at its periphery, but to no longer return to its initial position when the drive device is deactivated, due to the friction between the periphery and the wall, thus leaving the valve leaky. In order to obviate this problem, advantageous examples of the valve comprise centering aids which simplify centering the valve membrane in the valve. Nub-like structures on the periphery of the valve membrane or the part of the valve wall facing the periphery of the valve membrane can for example serve to center it. In the resting state, these structures establish a punctate contact between the membrane and the wall. When the valve is opened by deforming the membrane, the contact is lost due to the deformation, such that frictional forces cannot prevent the membrane from returning to its initial position. At least three such structures are necessary in order to correctly center the typically circular membrane. Because of how the valve membrane and valve space are dimensioned, two of the at least three structures typically touch the wall or the periphery of the membrane, respectively, once the membrane has been inserted, since the inner diameter of the interior space of the valve is chosen to be larger than the outer diameter of the valve membrane.

In one example, the adapter has an arcuate shape, i.e., the connecting needle is arranged coaxially with respect to the receiving compartment when the adapter is inserted and the opening for the catheter projects about 90° from the axis of the receiving compartment. In one advantageous arrangement of the opening, the catheter is guided out of the opening obliquely relative to the lateral edges of the administering apparatus. This has ergonomic advantages for the person using the device.

In one example, the adapter can only be placed onto the administering apparatus in a particular and unambiguous orientation.

An infusion device is presented for infusion of a fluid into a body from a replaceable reservoir, such as a carpoule or ampoule, which is connectable to an infusion set adapter at a connecting site of the infusion device, which connecting site can be located above an inserted carpoule or at any other convenient location as long as a connecting element or cannula of the infusion set adapter can be connected to or fluidly coupled with the substance or fluid to be infused. The infusion device comprises a drive mechanism, such as a motor with or without an encoder preferably coupled to a gear system, bearings and optionally elements or sleeves to drive a driving element, such as a piston rod, to operatively couple with at least portion of the exchangeable reservoir or carpoule, which portion can for example be a plug slidably positioned within the carpoule and causing the delivery of the substance or fluid contained within the carpoule when pressed towards a delivery opening of the carpoule. In one example, the gear system comprises sleeves and gearing wheels and is constructed such that meshing teeth structures from interacting wheels are made from non-equivalent materials for improved tribological and gear performance. The materials used for the gear system can be, but are not restricted to, plastics with or without fiber reinforcement (PEEK, Polyamides, Polyesters, PPSU, PSU, POM, PE, PP, UHMWPE, polyetherimides, thermosetting epoxies, glass fiber or carbon fiber reinforced), metals (brass, cupper, iron, steel, chrome nickel steel, cobalt-chrome molybdenum alloys) or ceramics (aluminium oxide, zirconium oxides or mixed ceramics). The infusion device comprises a housing which can be made of plastic or any other kind of material to preferably be impermeable for water or to be water resistant and to further preferably be air tight. The housing can comprise a compartment or closed area which is at least partially or fully surrounded by a part of the housing, such as exterior or outer and inner housing walls, to protect the elements within this housing compartment from external influences, such as external liquids. The housing is formed or sized to contain at least a portion of the reservoir or carpoule in a carpoule compartment. The housing may also be supported in its mechanical stiffness by other parts of the drive system or electronic unit such as the battery compartment. The housing is made from a polymeric material, preferably from polyester. In an alternative example, the housing is made from a material that is transparent for visible light and/or infra-red radiation. The housing may be completely or partially transparent for the radiation. The drive mechanism is at least partially or fully contained within the housing or contained within an enclosed compartment of or inside the housing. The drive mechanism compartment can be separated from the carpoule compartment using specific separation elements, such as, e.g., a drive housing and/or sealing elements or devices. An electronic control circuitry coupled to the drive system to control infusion of the fluid into the body and/or a battery compartment can also be arranged within the same compartment, e.g., the drive mechanism compartment or a different or further separate compartment inside the housing, so that the housing compartment or compartments enclose or surround at least a portion of the reservoir, preferably separated therefrom, e.g., by an air permeable seal, at least a portion or all of the drive mechanism and optionally the control circuitry or the battery. A sealing device is provided which permits the passage of air into and out of the housing or from the interior to the exterior of the housing and vice versa or to the enclosed mentioned compartment(s) and inhibits the passage of liquids into the housing or the housing interior or into at least one of the enclosed compartment(s), such as the drive mechanism compartment. The sealing device can be a single or can be several separate sealing elements and is arranged at the drive mechanism or a part thereof or at a location between a part of the drive mechanism and the connecting site of the infusion set adapter or at the connecting site of the infusion set adapter. The sealing device or one or more sealing elements of the sealing device are preferably located along a path through which air can flow or can be exchanged between the inside of the housing, such as the drive mechanism compartment, and the outside of the housing in order to seal this path and preferably to prevent the intrusion of external liquid or water and preferably also to prevent the leaking of a fluid to the outside of the housing. Any opening or path, such as at the battery compartment, at a function key, at or around the display can be sealed with such a sealing element. The sealing device or an element thereof which can be considered to be permeable for air is preferably arranged inside the housing, for example, between the carpoule compartment and the drive mechanism compartment, but can also be arranged at an opening of the housing to the exterior, such as an opening provided in the housing to which an infusion set adapter can be connected and/or at which a carpoule can be inserted into the housing or can be exchanged or replaced.

The sealing device which permits the passage of air into and out of the housing or a housing compartment and inhibits the passage of liquids into the housing or a housing compartment through the sealing device can be arranged at or in any path from the inside of the housing or the housing compartment to the outside of the housing or to a neighboring compartment being on a path to the outside of the housing and can for example be a sealing device which will be present at any known location in any prior art infusion device, however, being modified or made from a material to permit the passage of air into and out of the housing or a housing compartment and inhibit the passage of liquids into the housing or a housing compartment. For example a sealing device being provided at an opening or surrounding the cover of a compartment, such as the cover of the battery compartment, can be made to be air-permeable and liquid-impermeable. In addition or alternatively, a sealing device provided at a function key, such as a sealing device for example surrounding the function key itself or encompassing a function key unit to shield the housing's interior can be made from a material being permeable for air and impermeable for liquids. Alternatively or in addition, a sealing device being provided to seal the gap or opening between the display and the neighboring housing can be made to be air-permeable and impermeable for liquids. The sealing device or at least an element thereof is preferably arranged between an inner area of the infusion device in which inner area for example at least a part of or the whole drive mechanism and/or optionally one or more of the reservoir or carpoule or electronic control circuitry or battery is located and which is enclosed by at least a part of the housing, which part can also comprise or be an internal and/or part or wall of the housing, and an outer area of the infusion device, wherein the carpoule compartment or reservoir area of the infusion device can optionally or partly be seen as belonging to the outer area of the infusion device. Going from the outside or the exterior of the infusion device or housing to the inside, one may pass optionally a sealing device or an element thereof, the carpoule compartment, optionally a sealing element, the drive mechanism, optionally a sealing element, optionally an electronic control circuitry and optionally a battery. The path from the outside to the inside needs not to be on a straight line and can be curved inside the housing and may have a "U"-shape, as shown in FIG. 2a, for example. The drive mechanism may include a driving element, such as a motor being driven by electricity or other means, such as pressurized air. The drive mechanism may include a gear system connected to the motor including, e.g., gear system toothed wheels. A drive housing may be provided as part of the drive mechanism, which drive housing may separate the drive system compartment being interior of the pump from other compartments or the exterior. The drive housing may have an opening through which a driven element such as a piston rod may pass or advance.

The housing does preferably not contain a vent port, such as for example a vent port 8 shown in the enclosed FIG. 2a, for example, or a vent port as described in the mentioned U.S. Pat. No. 7,597,682 B2. However, optionally such a vent port can be provided in an infusion device, although such a vent port being an aperture of the housing with the sole purpose to permit the passage of air into and out of the housing or between the drive mechanism compartment and the carpoule compartment is no longer required The sealing device or at least an element thereof preferably consists of a hydrophobic and/or lipophobic or oleophobic material that permits the passage of air into and out of the housing and inhibits the passage of liquids into the housing. Such a hydrophobic or lipophobic material can be formed from Polytetrafluoroethylene (PTFE), microporous expanded PTFE (ePTFE), High-density polyethylene (HDPE), Polyethersulfon (PES), polydimethylsiloxane (PDMS), Polyetherester, Ultra-high-molecular-weight polyethylene (UHMW) polymers and can for example be Gore-Tex®, Polyphobe™, Porex®, Sympatex, eVent fabrics, Filtrone, polyurethane foam or porous plastic.

The sealing device or at least a sealing element can be attached to the housing and/or to the infusion set adapter using adhesives, sonic welding, heat welding or molding or any other method to provide an adhesive bond or a form fit.

Preferably the sealing device or a sealing element allows the air pressure within the housing or within a compartment of the housing, such as the drive mechanism compartment, to equalize with the air pressure outside of the housing or a compartment on the path to the outside, such as the carpoule compartment, for example by permitting a certain amount of inside air to pass through the sealing device or sealing element to the outside or neighboring compartment in case the air pressure inside the housing is higher than that on the exterior side or vice versa in case the outside air pressure is higher than the pressure in the inside, which inside might be the compartment in which at least parts or all elements of the drive mechanism and/or optionally the carpoule or electronic control circuit or battery is arranged. The air pressure equalization is thus not guaranteed by a separate opening in the housing but instead by the sealing device or sealing element being located along a path from the outside to the inside of the compartment or housing, as mentioned above.

The sealing device or a sealing element can be formed as an O-ring, a gasket ring or a seal ring or can have any other shape to seal the mentioned path from the outside to the inside of the housing. One or more sealing elements can be provided within or at the housing and/or within or at the infusion set adapter.

A sealing element, such as a sealing ring or O-ring, can be provided between an inner side of the housing or an integral part of the housing, such as a viewing window, and a part of the drive mechanism, such as for example a drive housing, to permit the passage of air and to inhibit the passage of liquids. Another preferred location for a seal is on the carpoule compartment, such as on the inner side thereof, preferably at a distal side of the carpoule compartment, so that this seal may on the opposite inner side be in contact with a proximal housing of the infusion set adapter when placed or fixed onto the infusion device. A further preferred location for the sealing element or the sealing device is at the infusion set adapter, such as on the outside of an outer wall of the proximal housing of the infusion set adapter.

More than a single sealing element can form the sealing device and it is also preferred that for example two sealing elements or sealing rings are provided at the adapter and/or at the infusion device, preferably at the aforementioned locations and having an axial offset, such as being spaced apart in a dispensing or administering direction of the substance to be infused. It is also possible to combine the provision of a single or more sealing element at the infusion device and one or more sealing elements at the infusion set adapter. In case two or more sealing elements are provided along a gas exchange path, it is preferred that all sealing elements are permeable for air and at least one or all are impermeable for water.

An infusion set adapter is connectable to an infusion device for infusion of a fluid from a reservoir into a body, which infusion device can be any of the aforementioned prior art infusion devices or infusion devices. The infusion set adapter comprises a sealing device having at least a single sealing element which permits the passage of air into and out of the housing and inhibits the passage of liquids into the housing through the sealing device when the infusion set adapter is connected to the infusion device. In case the carpoule is inserted into the infusion device or needs to be replaced, the infusion set adapter is removed from the infusion device, the insertion of the filled carpoule takes place and then the infusion set adapter is placed at the connecting site on the infusion device and is preferably locked with the infusion device, for example, by a bayonet lock. The carpoules are often made from glass and are subjected to relatively large dimensional tolerances. The dimensional tolerance for the length of the carpoule is compensated in the current device by a resilient member present either at the infusion adapter and/or at the receiving site of the carpoule compartment in the infusion device. The sealing element or sealing device is then arranged at a location which prevents in the state of the infusion set adapter being connected to the infusion device that liquid can pass from the outside of the infusion device to the inside and thus shields or protects for example the drive mechanism and/or the carpoule from getting into contact with liquids on the exterior side of the infusion device.

The carpoule plug (or stopper) is moved forward in the carpoule during administration of the medication by a cap flange contacting the plug. The plug and the flange are preferably not mechanically connected to each other and an air pocket maybe present between the plug and the flange. During exchange of a carpoule, the contact between the cap flange and the plug first will be released, whereas upon insertion of a new carpoule, the contact will be established. The formation of the air pocket between the distal end surface of the plug and the distal contact surface of the plug during exchange of a carpoule may be facilitated by the design of the cap flange. In one example the cap flange is modified for easy removal from—and insertion into—the carpoule plug during exchange of an empty carpoule by enabling air flowing into or out of the air pocket, respectively. The axial position and movement of the carpoule plug in the carpoule can be viewed through a viewing window that is part of the housing of the administration device. In one example, the viewing window is a smart window that adjusts the color or darkness depending on the specific ambient conditions. This ensures that the medication in the carpoule is protected from any adverse effects related to the absorption of light radiation and/or an increased temperature.

The exposure of insulin to UV radiation reduces its potency due to degradation, dimerization (Correira M. et al., UV-light exposure of insulin: Pharmaceutical Implications upon covalent insulin dityrose dimerization and disulphide bond photolysis, PLOS One, Vol 7 (12), 2012) and denaturation of the protein molecules. It is therefore an object to protect the insulin from UV exposure. This is achieved in WO 2006/061170 by adding an extra light cover shield which can be moved in front of the viewing window of the infusion device. The cover is made from a non-transparent polymeric material and once the cover is switched in front of the viewing window, the UV radiation is blocked and cannot reach the medication, e.g., insulin in the carpoule. The shield is an integrated part of the device and calls for a complicated mechanical construction since the shield needs to be rotatably or translationally mounted to the cap of the injection device. The user must be able to move the shield in order to view the remaining amount of insulin available in the carpoule. As an alternative, ultra-violet (UV) absorbers can be added to the viewing window of the infusion device. Such molecules absorb light in the UV range (UVA, UVB or UVC) range and do not have an absorption maximum in the visible wavelength range, e.g., the viewing window remains in principle transparent and colorless. Often light absorbers (dyes, pigments) in the visible wavelength range are added to cover part of that wavelength range as well and to protect the medication from visible light absorbance, UV exposure and an increase in temperature. Adding such absorbers to the viewing window results in a permanent coloration and has the disadvantage that the visibility of the carpoule containing the insulin that is located behind the window is hindered, especially during the night or twilight. It is therefore an object to provide a UV/Visible light protection to the medication that provides a non-permanent, photochromic coloring or darkening depending on the ambient light conditions. It is intended to be dark and light-absorbing when exposed to visible light/UV radiation and colorless when not exposed to UV radiation. The medication is thus protected from UV/light degradation without compromising the visibility through the window in a darkened environment. Such photochromic effects are known in the art and provide a reversible transformation from a dark (absorbing) to a transparent (non-absorbing) state depending on the presence or absence of UV radiation. The photochromic molecules can be embedded in the viewing window of the delivery device as described in WO 2011/080092, with the purpose of providing an anti-counterfeiting identification and/or aid during the assembly of the components by increasing the visibility of parts when needed. As an alternative, the photochromic molecules can be applied as a coating material to the viewing window of the infusion apparatus or the photochromic molecules are a part of an adhesive label that is applied to the viewing window. Optionally, the label contains additional information about how to use of the apparatus, type of infusion apparatus, manufacturer identification, type of medication and any other information that is beneficial for the user, health care provider or manufacturer of the apparatus. The photochromic molecules are coated or printed on the label or the molecules are embedded in the label material itself or they are part of the adhesive between the label and the viewing window of the infusion apparatus. Such an adhesive label can be glued onto the outside or inside of the viewing window but it can also be glued on the outside of the carpoule containing the medication. The advantage of the adhesive label on the outside of the viewing window is that it provides an additional protection against scratching of the viewing window. The UV/light protection for the viewing window based on reversible photochromic effects can also be extended to the fluid path of the medication, e.g., the adapter, the tubing or cannula. The compartment for the carpoule can have a light source which facilitates viewing the content of medication in the carpoule. The light source preferably is a LED, OLED and the light can be distributed along the compartment using backlighting systems such as light guides or optical fibers. The user interface encompasses a touch screen display and the tactile menu control is based on tapping or sliding finger movements. The display is a multi-touch display whereby the system can be programmed that the first finger contact (e.g., on an icon or value) activates a new screen or modifies the current screen display without allowing a second contact to activate another icon or change a value simultaneously. The software is programmed such that the first contact activates one parameter or module and de-activates other areas or functions on the display that could be activated at the same time. In another example the multi-touch functionality of the display is used and the system is programmed to allow for more than one finger touch activation at a time. The user interface can be adjusted to the individual needs of the user, for example the visual presentation of the icons is more oriented to a left-handed respectively right-handed user, or a user carrying the device on the left side or right side of the body, and the icons can be rotated 180° accordingly.

The user interface with the touch screen display and/or the activation button has a feature to prevent unwanted activation of icons by accidental touching or sweeping of the display screen. The touch screen must be unlocked before critical parameters or functions, actions of the infusion apparatus can be modified or initiated. The unlocking of the touch screen is done by typing a code on the screen and/or using an activation button or function key. The touch screen is automatically locked after a time out period (typically up to 2 minutes, preferably between 5 and 35 seconds) or by pressing the function key, depending the user interaction with the menu.

A wireless or telemetric communication between the infusion apparatus and an external device may exist. The infusion apparatus can send or receive data to an external device via a wireless, preferably low energy Bluetooth connection. The wireless connection can both be used during set-up of the device at the manufacturer or during use by a patient or health care professional. There can be several authorization levels for exchanging data such as status, commands, error messages, the history file or uploading or downloading software. A different authorization profile may exist for the patient, the medical doctor, a health care professional (HCP), a hospital or the manufacturer of the apparatus, respectively.

The infusion apparatus is used often but not solely by patients that have diabetes. Insulin dosing that is too high or too low can lead to a hypoglycemic or a hyperglycemic stroke, respectively. The patient can lose consciousness, collapse and need special care by a HCP to prevent further harmful or even dangerous to life complications. It is therefore an object to identify a stroke and/or collapse of the patient, identify the geographical position of the patient and send an emergency signal to an external receiver using the wireless communication to provide data on the location and/or medical history of the patient.

The infusion apparatus reports a signal from a sensor dedicated to measure accelerations that are typically attributed to a falling patient. This sensor maybe identical to the acceleration/impact sensor described above or it is a separate sensor unit. The infusion apparatus furthermore comprises a positioning sensor such as a GPS that enables accurate identification of the geographical position. Such a GPS sensor is described in WO 2009/035759 where position and movement of the patient are recorded and the data are used to identify the activity level of the patient. The activity level can be linked to the dosage of the insulin thus increasing or decreasing the insulin dosage depending on the activity level of the patient (e.g. sports). In US 2008/0269673, the administering device and therewith the patient data can be monitored via remote control and the appropriate personnel can react when they identify any abnormal activity or behavior. The device is equipped with GPS sensor so the appropriate personnel can locate the patient when needed. In the present invention, in the case of a collapse of a patient, the acceleration sensor of the device sends a signal to the processing unit and triggers an alarm that is sent together with the identification and GPS position of the patient to an external receiver. Thus the trigger for any action is not done via people monitoring the data externally but directly by the device. The receiving unit responds accordingly and initiates actions to prevent damage to the patient.

A method of equalizing pressure in an infusion device for infusion of a fluid from a reservoir into a body, the infusion device being connectable to an infusion set adapter at a connecting site, the infusion device comprising a drive mechanism to operatively couple with at least a portion of the reservoir, a housing being sized to contain at least a portion or all of the drive mechanism comprises the steps of: Providing a seal in a path from inside the housing to the outside of the housing which seal permits the passage of air into and out of the housing or drive mechanism compartment and inhibits a passage of liquids into the housing to equalize the air pressure inside the housing with the air pressure outside of the housing.

BRIEF DESCRIPTION OF THE DRAWINGS

FIGS. 3a-3g are illustrations representing a drive train according to certain implementations;

FIGS. 3h-3j illustrate details of a force sensor unit and a closing cap according to certain implementations;

DETAILED DESCRIPTION

In order to specify the directions within the administering apparatus, designated directions are defined as follows. The distal direction is respectively understood to mean the direction in which the liquid and the drug plug are moved when the drug is administered. As will be described again in more detail below, liquid in the liquid path is diverted in the interior of the administering apparatus and changes its flow direction. The distal direction therefore corresponds to different absolute spatial directions for different parts of the administering apparatus. The proximal direction is correspondingly defined as the opposite direction to the distal direction. A lateral direction is a direction perpendicular to this.

FIGS. 1 to 6 show an embodiment in accordance with the invention of the device for administering a fluid product. The embodiment shown in the figures is intended to describe the invention by way of an example. Other embodiments have already been described in part further above and/or are mentioned repeatedly in the text of the description of the figures, and additional possible embodiments will be apparent to the person skilled in the art on the basis of the description of the invention, such that the embodiments described below are not to be regarded as limiting.

Figure 1A:
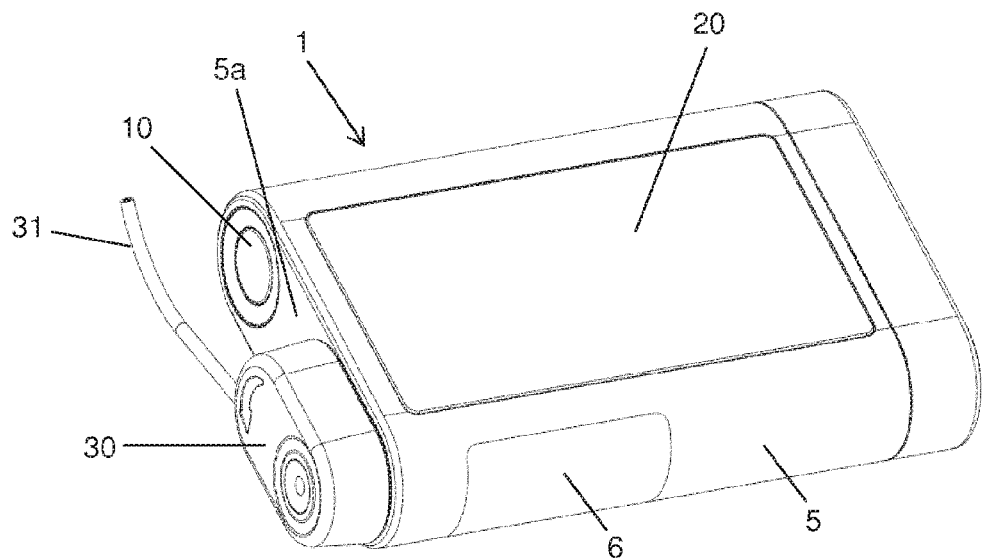
FIG. 1a is a first exterior view of a device in accordance with the invention.
Figure 1B:
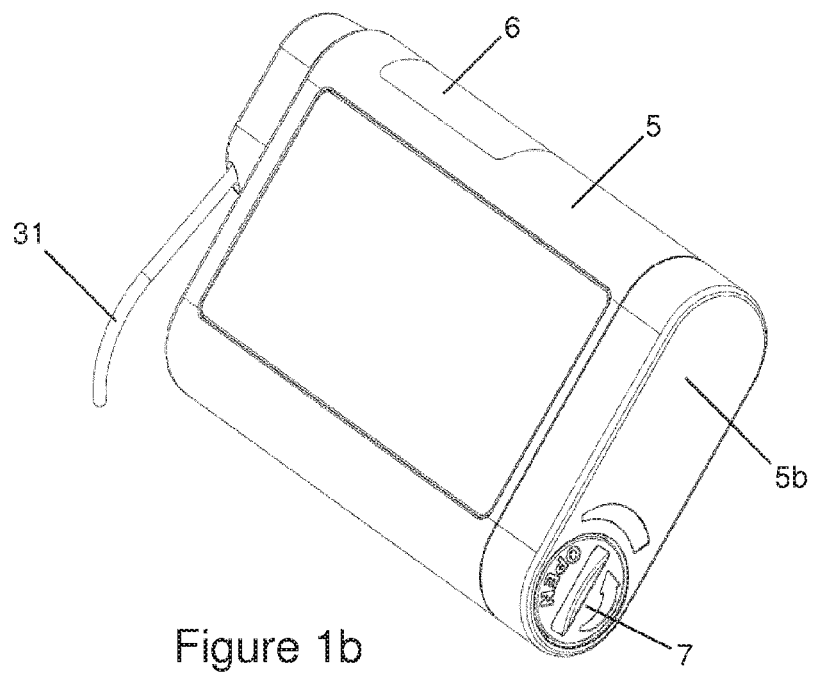
FIG. 1b is a second exterior view of the device in accordance with the invention.

The device shown in FIGS. 1a, 1b and 2 comprises the administering apparatus 1, shown here as an infusion pump, and the infusion set, wherein only the infusion set adapter 30 and the infusion line 31 of the infusion set are shown. The front side of the administering apparatus 1 is shown in FIG. 1a, and the rear side in FIG. 1b. A touch display 20 is arranged on the front side and comprises at least a display device, in particular an OLED or AMOLED, and a touch-sensitive surface arranged over the display device, in particular a touch screen, wherein the touch display 20 is sunk into the housing 5 of the administering apparatus 1, such that it ideally forms a continuous and smooth surface with the surface of the housing 5, wherein the touch display 20 is adhered or fused to the housing 5 or at least joined to the housing 5 in such a way that the join is closed in a liquid-proof seal.

Figure 5:
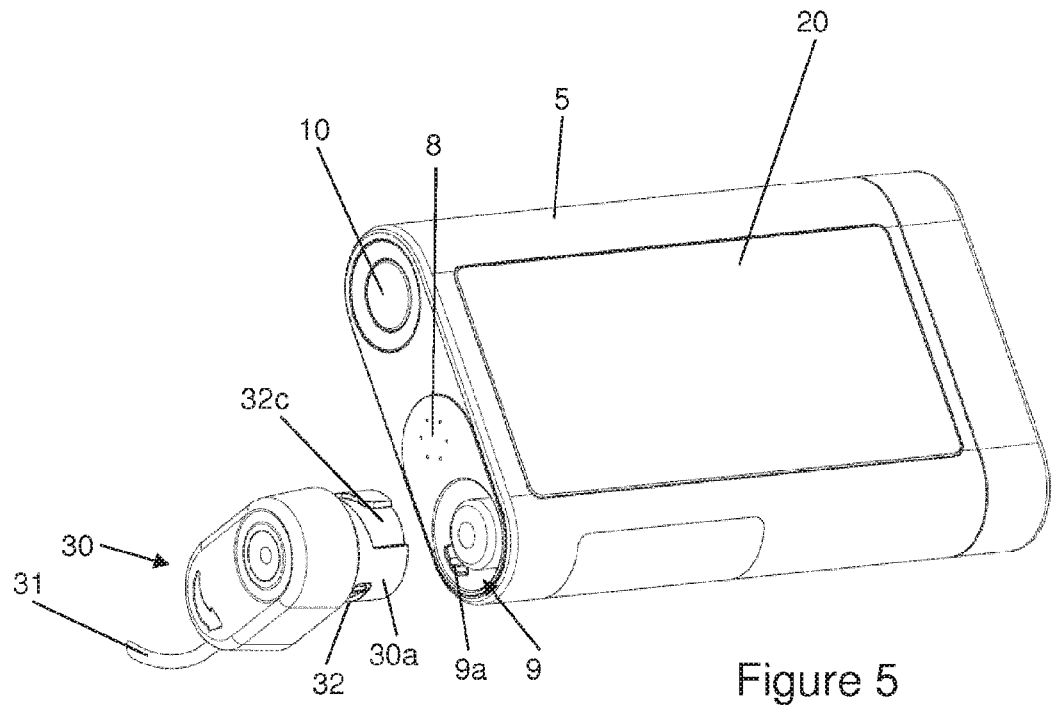
FIG. 5 illustrates a representation of the infusion set adapter and a receiving compartment according to certain implementations.

The viewing window 6 is arranged in a side wall of the housing 5 and can be considered as being an integral part of the housing 5 and enables the person using the device to view the carpoule compartment 9. The function key 10 is arranged on the distal wall 5a. As shown in FIG. 5, other elements are arranged on the distal wall 5a, namely the opening of the carpoule compartment 9 on the one hand and the device 8 for ventilating or evacuating the housing on the other. The latter enables the pressure to be equalized between the outside and inside of the administering apparatus 1. In the example shown in FIG. 2a, the ventilating or evacuating device 8 comprises a membrane 8a which closes an opening 8d of the housing. The membrane 8a allows gases to pass through but prevents liquid from passing through and is made, for example, from a porous PTFE membrane with pore sizes ranging from 0.1 to 10 micrometer, preferably from 1 to 5 micrometer, more preferably of 2 micrometer. The membrane 8a is protected against damage from without by an evacuating protection 8b. So as not to obstruct the exchange of gas between the inside and outside of the housing, the evacuating protection 8b comprises apertures 8c or holes.

Figure 2A:
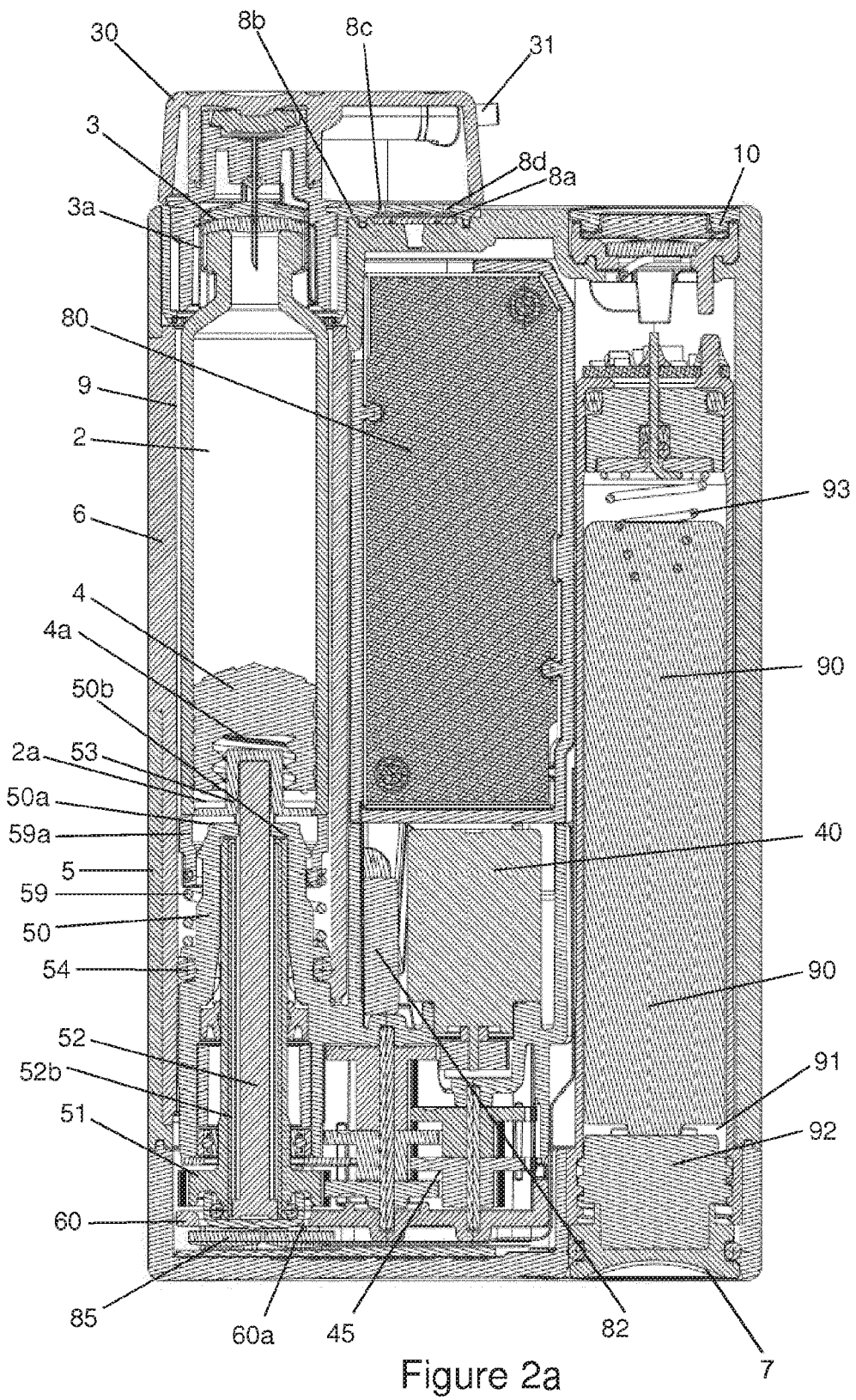
FIG. 2a is a section view of an administering apparatus together with an adapter according to certain implementations.
Figure 2B:
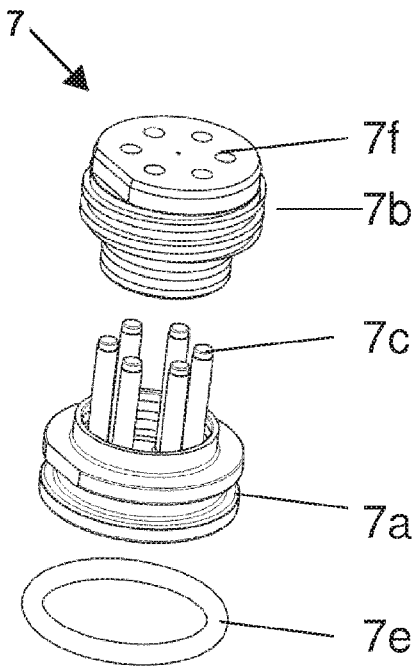
FIGS. 2b-2e are illustrations representing a battery compartment lid (FIGS. 2b and 2c), a battery compartment (FIG. 2d) and a cap flange (FIG. 2e) according to certain implementations.
Figure 2C:
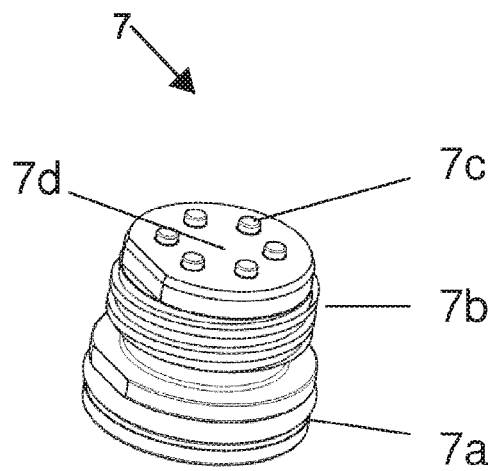
Figure 2D:
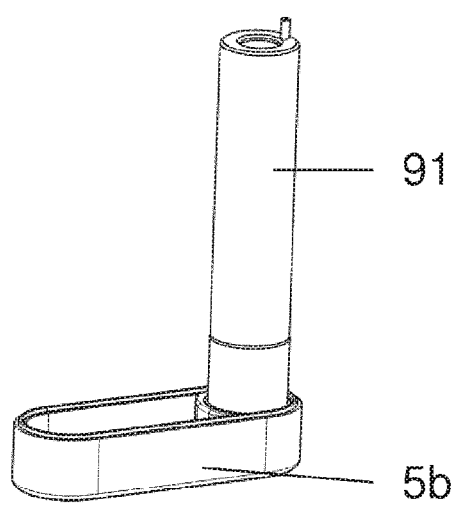
Figure 2E:
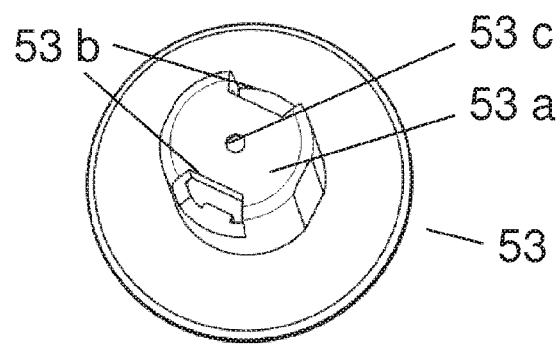
Figure 3G:
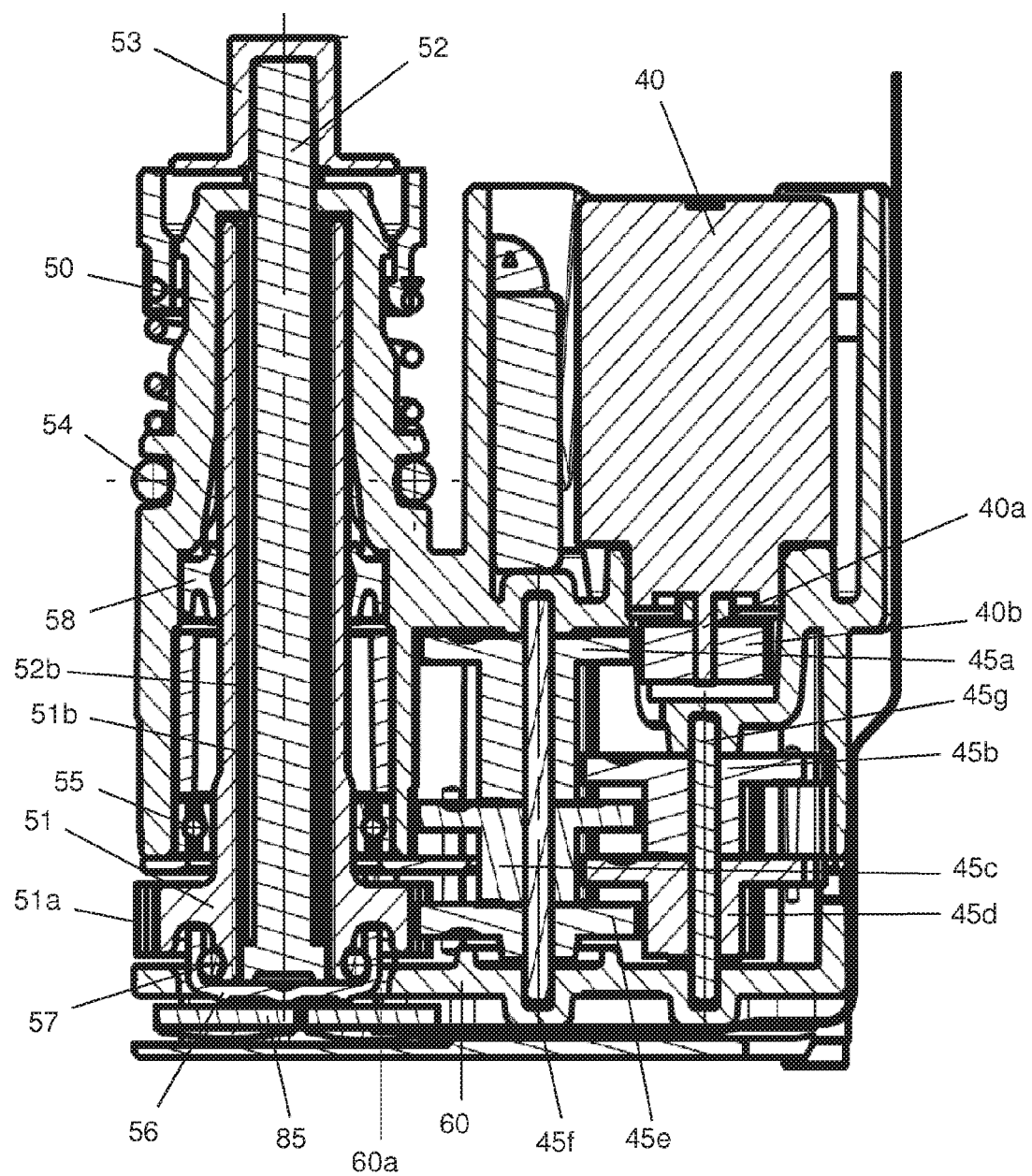

FIG. 2a shows the carpoule compartment 9 in section. The carpoule compartment 9 serves to accommodate the product container—in the case shown, the carpoule 2—wherein the carpoule 2 is introduced into the carpoule compartment 9 with its open end 2 first. The opening of the carpoule compartment 9 is closed by means of the infusion set adapter 30, as shown in FIG. 1a and FIG. 2a. The carpoule 2 is fixed between a proximal end of the infusion set adapter 30 and a distal end of a sleeve 59a which is axially displaceable and pressed into the distal direction against the proximal end of the carpoule 2 by a carpoule spring 59. The dimensional tolerance for the length of the carpoule 2 is thus compensated for by the sleeve 59a in combination with the spring 59. A battery compartment 91 may be constructed from a metal, preferably from nickel plated brass. The opening of the battery compartment 91 is arranged in a proximal wall 5b of the housing 5. The opening of the battery compartment 91 can be closed and opened by means of a battery compartment lid 7, wherein the battery compartment lid 7 is formed such that it can close the battery compartment 91 in a water-proof but, e.g., gas-permeable seal. A proximal part 7a of the compartment lid 7 is made of a plastic material covered with a metal cap 7b, preferably a nickel plated brass cap on its distal end (FIG. 2b, FIG. 2c). The plastic part 7a is connected to the metal cap 7b, preferably during the injection molding process or via ultrasonic welding. The metal cap 7b of compartment lid 7 can be threadedly engaged with the proximal end of battery compartment 91 for closure of the compartment after insertion of a battery. The electrically conducting battery compartment thus forms an electrically conducting contact with the battery lid 7 and both are part of the electrical circuit system. The battery lid 7 also prevents reverse poling of the battery due to reverse insertion of the battery. The metal cap 7b of the compartment lid 7 contains a plurality of holes 7f (for example 6) which are protruded by the underlying plastic material to form a plurality of plastic protrusions 7c. The plastic protrusions 7c are arranged such that the positive terminal of a battery can contact the surface 7d of the metal cap between the protrusions leading to an electrical contact between the compartment lid 7 and a primary cell 90 (e.g., battery). The negative terminal of a battery touches the plastic protrusions 7c of the compartment lid 7 and therefore no electrical contact exists between the negative pole of the primary cell 90 and the compartment lid 7. The compartment lid 7 thus can only form the positive contact terminal 92 of the device. The primary cell 90 can be introduced into the battery compartment 91, as shown in FIG. 2a, wherein the primary cell 90 can be a commercially available AAA battery (e.g. Alkaline) or alternatively a different type of battery or a correspondingly dimensioned rechargeable power pack (e.g. Lithium Ion, Nickel Metal Hydride NiMH). The battery lid 7 is used to close the battery lid compartment 91 after insertion of the primary cell 90. The sealing 7e which is part of the proximal part of the compartment lid 7 forms a waterproof barrier to the outside of the device. In order to obtain a good electrical contact between the primary cell 90 and the negative contact terminal 93 of the administering apparatus 1 and between the primary cell 90 and the positive contact terminal 92 of the administering apparatus 1, the negative terminal 93 can comprise or be formed as a spring, as shown in FIG. 2a, wherein the positive terminal 92 is fixedly attached to the battery compartment lid 7, such that when the battery compartment 91 is closed, a pressure force which optimizes the electrical contacting is applied to the contacts by the spring force. The battery compartment 91 is mechanically anchored to the proximal wall part 5b (FIG. 2d). The battery compartment 91 is made from a metal, preferably nickel plated brass, the proximal wall part 5b from a plastic material, preferably from a polyester. The mechanical anchorage is provided by and adhesive glue at the interface or by ultrasonic welding of the two parts or by injection molding the plastic part onto the battery compartment. The connection between the battery compartment 91 and the wall part 5b together with the mechanical stiffness of the battery compartment supports the strength and stiffness of the administering apparatus 1. The administering apparatus 1 shown in FIGS. 1a, 1b and 2 comprises a drive device. The drive device, which is also shown in detail in FIGS. 3a to 3g, comprises a motor 40, a gear system 45, a first conveying element, preferably advancing sleeve 51, and a second conveying element, preferably piston rod 52. In the administering apparatus shown, the advancing sleeve 51 can rotate but has limited axial movement versus the housing whereas the piston rod 52 is threadedly engaged with the advancing sleeve. The drive device also comprises a drive housing 50 in and/or on which the parts of the drive device can be mounted, wherein the drive housing 50 is fixedly connected to the housing 5. The seals 54, 57 and 58 seal the drive device off from the carpoule compartment 9 in a liquid-proof seal, in order to prevent liquid from crossing into the interior of the drive device. Seals 54, 57 and/or 58 can be made of a material which permits the transmission of air, as described above. The motor 40 is controlled and fed by an electronic control module 80. When activated, the motor axle 40a rotates and with it the driven toothed wheel 40b arranged rotationally fixed on the axle. The driven toothed wheel 40b transmits the movement onto the gear system 45. The movement of the motor is geared up or down in the desired ratio via the toothed wheels 45a to 45e of the gear system 45, wherein the toothed wheels 45a to 45e of the gear system 45 are rotatably mounted on the axles 45f and 45g, respectively. The gear system toothed wheels 45a to 45e comprise two coaxially arranged toothings which are arranged sequentially in the axial direction and such that they are fixedly connected to each other, wherein the two toothings typically exhibit a different number of teeth. The first toothing assimilates the movement from the preceding toothed wheel. The second toothing relays the movement to the next toothed wheel, wherein—as the person skilled in the art will be aware—the gear system can vary without deviating from the concept of the invention. In particular, a different number of toothed wheels in the gear system can be chosen and/or the number of teeth on a toothed wheel can be varied. At the output of the gear system 45, the toothed wheel 45e transmits the movement onto the toothing 51a of the advancing sleeve 51. The advancing sleeve 51 is rotatably mounted in the drive housing 50 with the aid of the ball bearing 55, wherein a roll bearing, needle bearing or a simple slide bearing would also be possible. The seal 58 is arranged between the drive housing 50 and the advancing sleeve 51 and seals the interior of the drive housing 50 off from the outside of the rotatable advancing sleeve 51. On its inside, the advancing sleeve 51 comprises an inner thread 51b which is in engagement with an outer thread 52b of the piston rod 52. The piston rod 52 is arranged coaxially with respect to the advancing sleeve 51 and coupled to it via the threaded engagement mentioned. The piston rod 52 also comprises two longitudinal guiding grooves 52a (FIG. 3d). The cams 50a of the drive housing 50 engage with these guiding grooves 52a and thus allow a movement of the piston rod 52 in the longitudinal direction of the piston rod 52 relative to the drive housing 50, but prevent a relative rotation between the piston rod 52 and the drive housing 50. If the advancing sleeve 51 is rotationally set in motion via the gear system 45, then the threaded engagement between the advancing sleeve 51 and the piston rod 52 in combination with the rotational lock between the drive housing 50 and the piston rod 52 generates an axial shift in the piston rod 52 relative to the drive housing 50, hence the piston rod 52 is also shifted relative to the housing 5. The advancing sleeve can rotate in 2 directions and depending on the direction there is an ejection movement or a resetting movement of the piston rod. During an ejection movement for administering a product, the piston rod 52 moves in the distal direction, during a resetting movement the piston rod 52 moves in the proximal direction. The described arrangement of the drive can be kinematically reversed, without deviating from the teaching of the invention. In such a reversal, the piston rod 52 would be mounted, such that it can be shifted but is secured against rotating, in the advancing sleeve 51 and would be connected to the drive housing 50 via a threaded connection. If the advancing sleeve 51 were then rotationally set in motion by the gear system 45, the piston rod 52 would also be rotated and consequently screwed in the axial direction via the threaded connection with the drive housing 50. An equally advantageous axial advance by the piston rod 52 could thus also be achieved using a kinematically reversed arrangement.

The gear system 45, the advancing sleeve 51 and the piston rod 52 are made from materials adjusted to their specific purpose in terms of the mechanical or tribological performance. The toothed wheels 45a-e are made from plastic materials and selected such that two meshing teeth are made from different materials. The materials used for the gear system can be, but are not restricted to, plastics with or without fiber reinforcement (PEEK, Polyamides, Polyesters, PPSU, PSU, POM, PE, PP, UHMWPE, polyetherimides, thermosetting epoxies, glass fiber or carbon fiber reinforced) and with or without friction modifier (e.g. TPFE), metals (brass, cupper, iron, steel, chrome nickel steel, cobalt-chrome molybdenum alloys) or ceramics (aluminum oxide, zirconium oxides or mixed ceramics). The advancing sleeve 51 can be made from the above listed materials but is preferentially made from a metallic material such as brass. The piston rod 52 is also made from one of the listed materials above, preferentially from a carbon fiber reinforced plastic for sufficient stiffness of the rod under compressive forces. A cap flange 53 is attached to the distal end of the piston rod 52 and can mechanically engage with the proximal end of a carpoule plug 4. In the example from FIG. 2a shown, the proximal side of the carpoule plug 4 comprises a piston rod receptacle as a blind hole 4a with an inner thread, which improves the engagement of the cap flange 53. In an example, a carpoule plug 4 with no blind hole 4a is also conceivable, wherein the shape of the cap flange 53 would be correspondingly adapted. For improved engagement of the cap flange 53 and the carpoule plug 4, a hole 53c is pierced through the distal front surface 53a of the cap flange and/or has one or more grooves 53b on its side wall so that the air present in the blind hole 4a can easily escape during engagement of the flange into the plug. For improved disengagement of the cap flange 53 from the carpoule plug 4 and to prevent any sticking due to a potential vacuum between the cap flange 53 and the carpoule plug 4, the cap flange 53 is pierced or has grooves 53b on its side wall for air to enter the gap between the carpoule plug 4 and the cap flange 53 (FIG. 2e). A cap flange 53 may thus be for advancing a plug 4 in a carpoule 2 comprising a hollow cylinder with a substantially closed distal end surface that engages or disengages with the plug 4, and a proximal rim with a diameter above the diameter of the hollow cylinder; characterized in that the front end surface and/or side walls of the cylinder have means that facilitate the engagement or disengagement of the cap flange 53 and the plug 4 during exchange of a carpoule 2. The front end surface 53a has a pinhole, a clearance hole, a pocket or a structured surface such as a rippled structure, honeycomb structure or the like. The side walls of the cylinder have pockets, grooves or rippled structures and there can be connecting structures or grooves between the front end surface and the side walls such as radially extending grooves (see e.g., FIGS. 3a, 3b, 3d and 3e).

As described herein, the carpoule 2 is arranged in the housing 5. When the infusion set adapter 30 is inserted into the housing 5, the carpoule 2 is mounted axially between the drive housing 50 and the infusion set adapter 30, wherein a carpoule spring 59 ensures, via a sleeve 59a which abuts the proximal end of the carpoule wall, that the carpoule 2 is pressed in the distal direction against the infusion set adapter 30. The carpoule 2 comprises a cylindrical body which is open at its proximal end 2a and tapers at its distal end and is closed by a septum 3, wherein the septum 3 is fastened to the distal end of the carpoule 2 by a septum holder 3a. The carpoule plug 4 is mounted, such that it can be axially shifted, in the carpoule 2 and forms a moving proximal closure of the carpoule 2, since it also forms a seal with the carpoule wall. When the infusion set adapter 30 is inserted into the housing 5, a connecting needle—shown as a cannula 33—pierces the septum 3 of the carpoule 2 and thus establishes a liquid connection between the infusion set adapter 30 and the interior space of the carpoule 2, such that liquid product can pass from the carpoule 2 into the infusion set adapter 30. Shifting the carpoule plug 4 by means of an axial movement of the piston rod 52 in the distal direction reduces the interior space of the carpoule 2 and displaces product from the carpoule 2 and thus conveys it into the infusion set adapter 30.

As mentioned further above, the advancing sleeve 51 is rotatably mounted in the drive housing 50. Axial movements of the advancing sleeve 51 are possible to a limited extent. The axial movement is limited in the distal direction by the closed end 50b of the drive housing 50. The movement of the advancing sleeve 51 is limited in the proximal direction by a bearing plate 60 which is fixedly connected, in particular screwed, to the drive housing 50. A circular opening 60a arranged coaxially with respect to the advancing sleeve 51 is provided in the bearing plate 60 and exhibits a diameter which is less than the diameter of the region of the advancing sleeve 51 which bears the toothing 51a, thus ensuring that the axial movement of the advancing sleeve 51 is limited by the bearing plate 60, despite the opening 60a.

The proximal end of the advancing sleeve 51 is closed by the closure cap 56, wherein the closure cap 56 is movably held on the advancing sleeve 51 by the seal 57—shown for example in FIG. 3g as an O-ring—which is arranged on the proximal end of the advancing sleeve 51, wherein the diameter of the closure cap 56 is chosen such that the cap 56 fits through the opening 60a in the bearing plate 60. A force sensor 85 is arranged, fastened to the housing on one side, between the closure cap 56 and the housing 5 of the administering apparatus 1, wherein "fastened to the housing" means in particular that the force sensor 85 is mounted such that it cannot be moved laterally relative to the housing 5. A certain clearance can, but need not, be provided in the axial direction, but which is eliminated when the drive device is put into operation. Said force sensor 85 measures forces which are transmitted from the closure cap 56 to the sensor 85. Due to the advantageous embodiment of the closure cap 56, the advancing sleeve 51 and the piston rod 52, various forces can be measured using the arrangement shown in FIG. 2a or FIG. 3g. On the one hand, the reaction force during the axial movement of the piston rod 52, in particular while product is being administered, can be measured, i.e. when the piston rod 52 is moved in the distal direction and presses against the carpoule plug 4, the advancing sleeve 51 exerts a force in the proximal direction which is transmitted onto the force sensor 85 via the closure cap 56. Measuring forces in this way enables occlusions, i.e., for example blockages, in the infusion set to be identified on the basis of an increase in force and/or a force limit value during delivery, wherein the measurement signal generated in the force sensor 85 can be evaluated and stored in the control module 80. In addition, when carpoules 2 are newly inserted, the position of the piston rod 52 at which the piston rod 52, in particular the cap flange 53, hits the carpoule plug 4 can also be identified; in this situation, an increase in the reaction force can again be observed at the force sensor 85. The measurement signals from the force sensor 85 are read and evaluated by the control module 80. Consequently, the control module 80 can for example stop the motor 40 and issue alarm alerts on the display or let the motor 40 continue running. On the other hand, it is possible to measure forces which are transmitted directly from the piston rod 52 to the force sensor 85 via the closure cap 56. When a new carpoule 2 is inserted into the administering apparatus 1, the piston rod 52 has to be moved back into its initial position before the new carpoule 2 is inserted. This is achieved by driving the motor 40 in the opposite direction to the delivery movement. Consequently, the corresponding rotation of the advancing sleeve 51 draws the piston rod 52 into the advancing sleeve 51, i.e. in the proximal direction. When the piston rod 52 reaches its initial position, it hits the closure cap 56 and presses it in the proximal direction onto the force sensor 85. The closure cap 56 can be considered to be a transfer element. The increase in force which the proximal movement generates can be measured by the sensor 85 and relayed to the control module 80. The control module 80 can then correspondingly stop the motor 40, and the new carpoule 2 can be inserted.

The reset of the piston rod 52 and the interaction with the closure cap 56 and the force sensor 85 is described in more detail herein (FIG. 3g). During rewinding of the advancing sleeve 51 and retraction of the piston rod 52 in the proximal direction, the proximal end surface of the piston rod 52 will touch the distal surface of the closure cap 56. The closure cap 56 is engaged with the advancing sleeve 51 through seal 57. The seal 57 is made from an elastomeric material and the closure cap 56 is snapped onto the seal 57 by snap-fit means, preferably by a circumferential groove in the inner wall of the closure cap 56. The connection between the closure cap 56 and the advancing sleeve 51 is therefore of resilient nature. The seal 57 rests in the circumferential grooves on the inside of the closure cap 56 and on the outside of the proximal part of the advancing sleeve 51. The grooves are shaped such that in combination with the clearance between the inside groove of the cap and the outside groove of the sleeve, a resilient force can be exerted by the seal 57 onto the cap which retracts the cap to the original or defined position before resetting the device. The seal 57 is preferably an O-ring made from an elastomeric material selected from the group of EPDM, silicone, PDMS, Polyurethane, Thermoplastic elastomers, Viton, Fluoroelastomers. The seal 57 is more preferably an O-ring made from a silicone with a Shore Hardness A ranging between 40 and 60, more preferably a Shore Hardness A of 50+/−5.

Figure 3H:
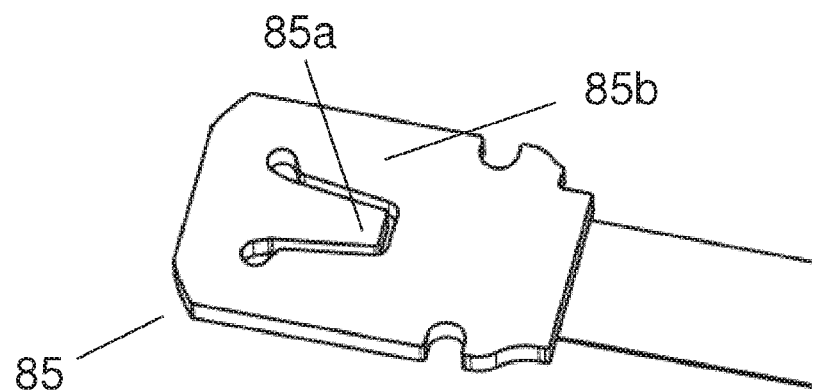

During continued retraction of the piston rod 52 after touching the closure cap 56, the piston rod 52 axially displaces the closure cap 56 in the proximal direction towards the force sensor 85 such that the closure cap 56 is axially displaced against the bias of a resilient element, preferably formed as the seal 57. The axial displacement of the closure cap 56 versus the advancing sleeve 51 is less than 1 mm, more preferably less than 0.5 mm, more preferably between 0.1 and 0.4 mm. The force sensor 85 comprises a cantilever beam 85a jointed to a base plate 85b and the cantilever beam 85a can deflect versus the base plate 85b (FIG. 3h). The beam is coated with a structured material (e.g., electrically resistive) that is sensitive to the deformation of the beam and enables a force measurement. Furthermore the base plate 85b surrounds the cantilever beam 85a without interfering with the deflection of the beam. The base plate 85b of the force sensor and the cantilever beam 85a are preferentially in a horizontal plane. The transfer element, i.e., the closure cap 56, further comprises a force transmitting element and a restricting element. Here, the proximal surface of the closure cap 56 comprises a force transmitting element and a restricting element, FIG. 3i. The force transmitting element, in this case a protrusion 56a, interacts with the cantilever beam 85a of the force sensor and ensures that the axial displacement of the closure cap 56 results in a deflection of the beam of the force sensor 85 for measuring the axial forces during reset of the piston rod. The force transmitting element thus transmits the axial forces during the reset operation whereby the closure cap 56 is axially displaced versus the advancing sleeve 51 and is deflecting the beam 85a of the sensor 85. During this reset, the restoring force on the drive train is governed, i.e., carried, by the distal end of the advancing sleeve 51 that is pushed against the closed end 50b of the drive housing 50. During normal operation of the infusion apparatus, the force sensor 85 measures the axial forces during delivery of the medication from the carpoule 2 and these forces are transmitted to the force sensor 85 via the force transmitting element 56a of the closure cap 56, but in this case the cap 56 is not axially displaced versus the advancing sleeve 51.

Figure 3I:
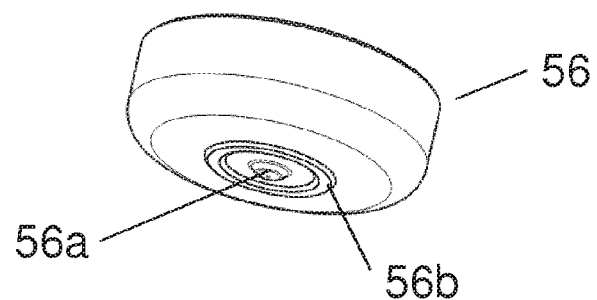

The restricting element, presented as a protruding ring structure 56b, interacts with the base plate 85b of the sensor. The protruding distances of the force transmitting element 56a and the limiting element 56b are selected such that the force transmitting element 56a deflects the beam of the force sensor prior to the restricting element 56b touching the base plate 85b and preventing any further deflection of the beam 85a of the force sensor. The difference in protruding distance of the force transmitting element and the restricting element is 0.2 mm, preferably 0.15 mm, more preferably 0.12 mm. In FIG. 3j-I, the transfer element does not displace or even touch the force sensor 85 and the force transmitting element 56a does not touch the cantilever beam 85a. In FIG. 3j-II, the transfer element has advanced and the force transmitting element 85a displaces the cantilever beam 85a but the restricting element 56b does not contact the base plate 85b yet. Upon further advancement of the transfer element, the restricting element 56b loads the base plate 85b of the sensor 85 and restricts the maximum displacement of the transmitting element 56a and therewith the deflection of the cantilever beam 85a (FIG. 3j-III). This implies that the ratio of the protrusion distances for the transmitting element 56a and the restricting element 56b is above unity. During axial movement of the closure cap 56, the transmitting element 56a first deflects the cantilever beam 85a before the restricting element 56b restricts the maximum beam deflection. The axial forces of the proximal movement of the piston rod 52 are measured and the forces increase with increasing beam deflection. Further movement of the transmitting element 56a is hindered once the restricting element 56b touches the base plate 85b of the force sensor 85. The restricting element 56b therefore restricts the maximum deflection of the beam 85a and governs the upper force limit of the force sensor 85 and protects the force sensor 85 from overloading and/or mechanical damage. The upper force limit of the sensor is 100N, more preferably 50N with a linearity between the applied force and the measured force up to 40N, more preferably up to 30 N. Above 30N, the deflection of the cantilever beam 85a may be hindered by the restricting element 56b interacting with the base plate 85b of the sensor. The maximum deflection of the cantilever beam is linked to the difference in protruding distances discussed above and amounts 0.20 mm, preferably 0.15 mm, more preferably 0.12 mm.

This construction is advantageous compared to the prior art where a separate back plate is needed to restrict the maximum deflection of the beam of the force sensor. The rewinding of the advancing sleeve and retraction of the piston rod is stopped once a certain force level (preferably below 30N, more preferably below 20N, more preferably below 10N) is reached and the rewinding of the advancing sleeve is stopped by the control unit. The piston rod is now accurately located in its most proximal position and the piston rod can be advanced by rotating the advancing sleeve over a controlled number of rotations into a predefined position whereby the cap 56 is retracted to its original position due to the resilient force exerted by the O-ring present between the cap and the advancing sleeve. During distal movement of the piston rod 52, the piston rod 52 moves away from the closure cap 56 which itself moves axially into the position prior to resetting the device due to the resilient forces induced by a resilient member, preferably by the seal 57 and therewith unloading the force sensor 85, e.g. there is no direct contact or minimal contact or no load-bearing contact between the force sensor 85 and the force transmitting element 56a or restricting element 56b (e.g., limiting element) of the closure cap 56 as shown in FIG. 3j-I. The beam 85a of the force sensor 85 is free floating after the reset of the device and this enables accurate calibration of the zero force setting of the force sensor unit before insertion of a new carpoule 2. Once the reset of the piston rod 52 is finished, a new carpoule 2 is inserted into the carpoule compartment 9 and the piston rod 52 is moved in the distal direction for priming the infusion set.

Figure 13:
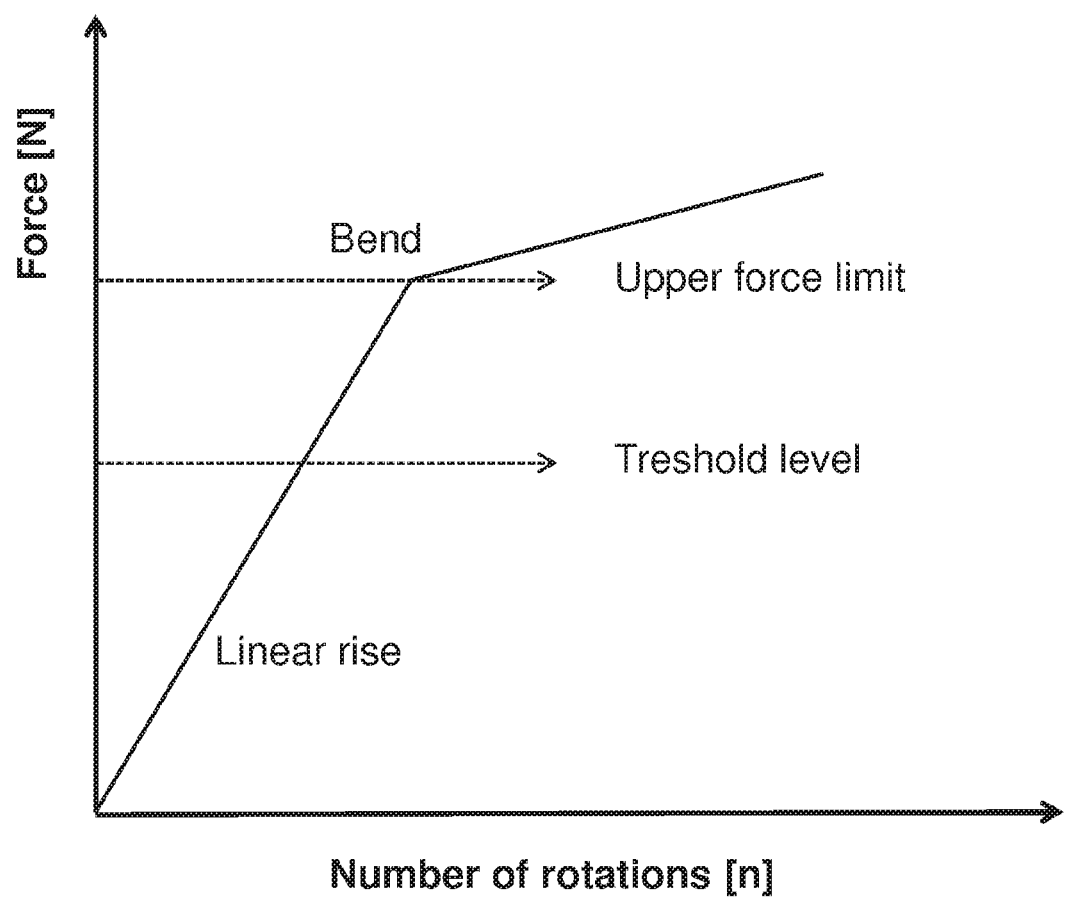
FIG. 13 is a schematic drawing of the force vs. rotations curve during reset.

It is an object of the present invention to precisely measure the upper and lower limits of the force measurement range. The accurate zero force setting is described above, the measurement of the upper limit is described as follows. The infusion apparatus is intensively used throughout the service life and this can lead to wear of the force transmitting element and/or the deflection beam of the force sensor. This will lower the ratio of the protrusion distance of the transmitting element versus the limiting element and therewith limit the maximum deflection of the deflection beam (e.g., cantilever beam 85a) of the force sensor 85 that can be achieved during reset of the piston rod 52. Thus during the service life the upper limit of the force limit that can be measured is potentially lowered and the measurement range reduced. During each reset the upper force limit is measured and stored in the control unit (e.g., electronic control module 80). The upper force limit is characterized by a non-linear rise, or a deviation from a linear rise or bend in the curve of the measured force versus the number of rotations of the advancing sleeve 51 (FIG. 13). If the upper force limit is below a predefined value, the safe operation is not guaranteed and an alarm message is sent to the user. For example with a reduced measurement range, the device cannot measure an occlusion, i.e., the upper measurement limit for the measurement range of the force sensor is below the threshold limit set for an occlusion force. The infusion set adapter 30, consisting of a proximal housing 30a and a distal housing 30b, can be detachably connected to the housing 5 of the administering apparatus 1. This is preferably achieved by the bayonet lock 32 shown in FIGS. 4, 5 and 6. The bayonet lock 32 consists of two guiding grooves 32b and 32c, which are arranged on the outside of the proximal housing 30a, and complementarily formed latching elements 9a (only one of which is shown in FIG. 5) in the carpoule compartment 9. The guiding grooves 32b and 32c are of different widths, and the two latching elements 9a (only one of which is shown) are correspondingly also of different widths—to fit the groove width of the guiding grooves 32b and 32c, respectively. The proximal housing 30a of the infusion set adapter 30 is formed such that it can be inserted into the carpoule compartment 9 and such that a cylindrical fit between the proximal housing 30a and the carpoule compartment 9 results. The latching elements 9a protrude in the radial direction into the interior of the carpoule compartment 9 and are accommodated by the guiding grooves 32b and 32c, respectively, when the infusion set adapter 30 is inserted and guide the movement of the infusion set adapter 30. Due to the different widths of the guiding grooves 32b and 32c and the complementarily formed latching elements 9a, the infusion set adapter 30 can only be inserted into the carpoule compartment 9 in precisely one orientation. FIG. 5 shows the infusion set adapter 30 and the administering apparatus 1 before the infusion set adapter 30 is connected to the administering apparatus 1, wherein the infusion set adapter 30 is already orientated such that it can be inserted into the carpoule compartment 9. Once the infusion set adapter 30 has been completely inserted, it is rotated in the present example by about 90° clockwise, in order to close the bayonet lock 32. This rotation is also guided by the correspondingly aligned grooves 32b and 32c which exhibit a corresponding bend. During this rotation, the infusion set adapter 30 is drawn slightly further again into the carpoule compartment 9, in order to generate an optimum closure. At the end of this rotation, the infusion set adapter 30 is detachably snapped onto the carpoule compartment 9 via latching cams 32a, in order to prevent the connection from being undesirably released, wherein a tactile or audible feedback which can be perceived by the person using the device is preferably generated during said snapping. The infusion set adapter 30 preferably does not seal the carpoule compartment 9 off air-tight, in order to allow pressure to be equalized between the carpoule compartment 9 and the environment. In another example, the rotational direction of the infusion set adapter 30 can also be reversed, i.e. can be anti-clockwise. Correspondingly, the run of the grooves 32b and 32c of the bayonet lock 32 would also be aligned differently. The rotational angle can also be more or less than 90°, as long as the adapter 30 can only be inserted into the carpoule compartment 9 in precisely one orientation.

In the example shown, the proximal housing 30a and the distal housing 30b are adhered to each other in a water-proof seal. Alternatively, they could also be fused, welded or ultrasonic welded to each other. The infusion set adapter 30 of the infusion set (which is not completely shown) establishes a liquid connection between the product container, corresponding to the carpoule 2 shown, and the infusion set, shown here schematically as an infusion line 31. To this end, the infusion set adapter 30 comprises a cannula 33 which serves to pierce the septum 3 of the carpoule 2. The cannula 33 is arranged in the interior of the proximal housing 30a. The proximal housing 30a exhibits an approximately cylindrical shape and is open in the proximal direction. When the infusion set adapter 30 is inserted into the carpoule compartment 9 (and the bayonet lock 32 is latched), the proximal housing is arranged between the distal end of the carpoule 2 and the wall of the carpoule compartment 9. The cannula 33 is arranged coaxially with respect to the proximal housing 30a. When the infusion set adapter 30 is inserted into the carpoule compartment 9, the cannula 33 pierces the septum 3 of the carpoule 2 which is inserted beforehand into the carpoule compartment 9. This establishes a liquid connection between the carpoule 2 and the interior of the infusion set adapter 30. The axial guidance of the infusion set adapter by the guiding grooves 32b and 32c followed by a rotational locking movement ensures together with the coaxial arrangement of the cannula 33 that the septum 3 is pierced transversally in the center of the septum without radial or inclined deflection.

Figure 4:
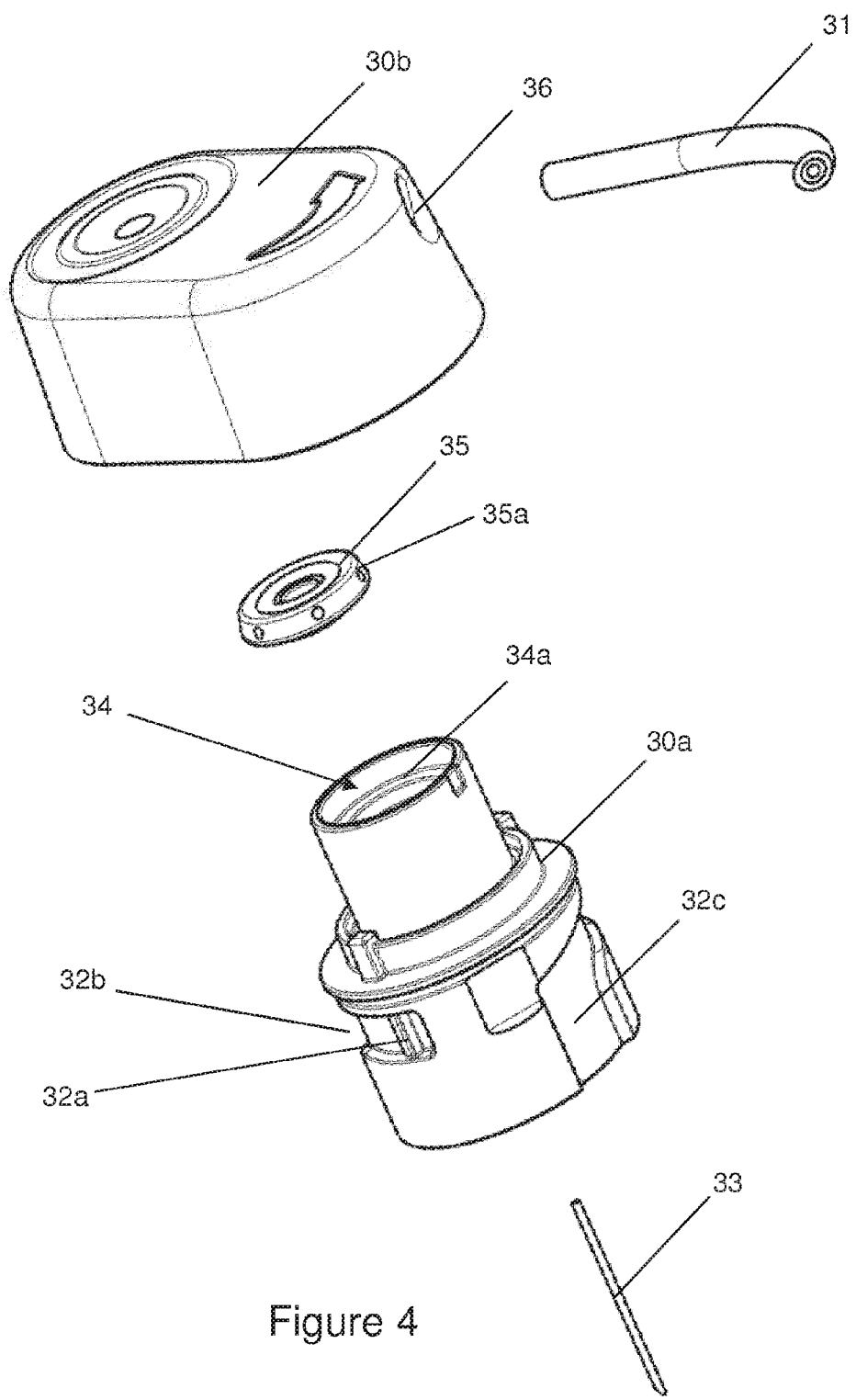
FIG. 4 is an exploded view of an infusion set adapter according to certain implementations.
Figure 6:
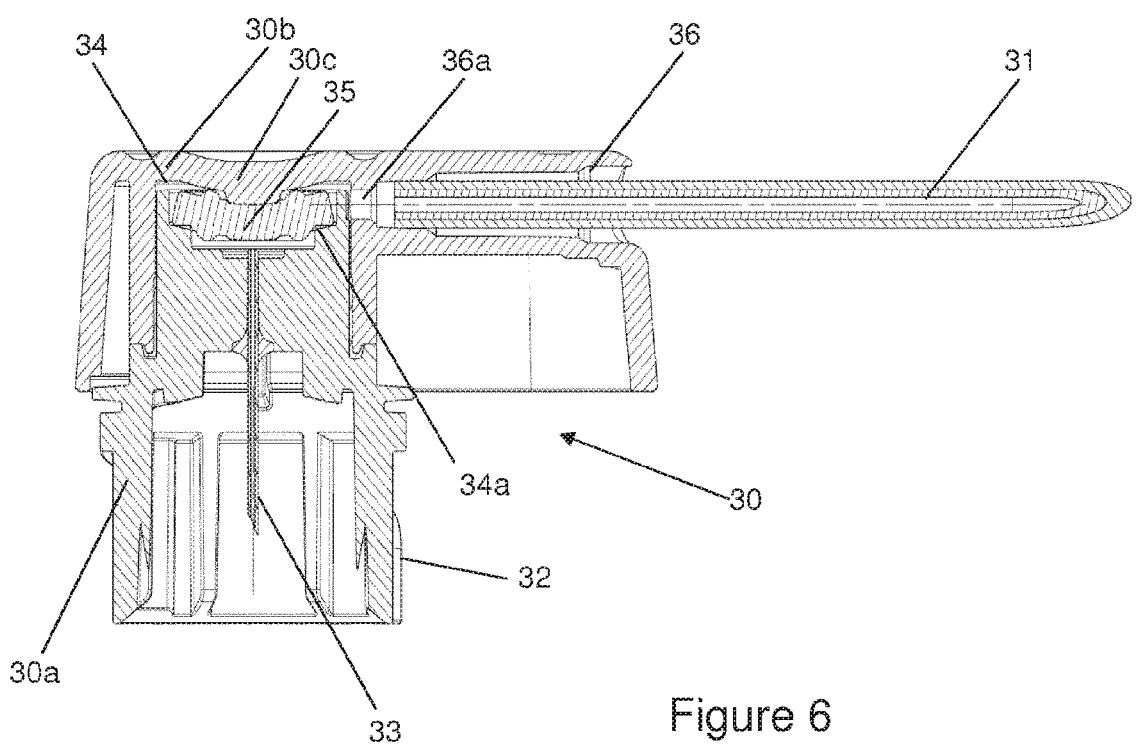
FIG. 6 illustrates a cross-sectional view of the adapter together with a valve according to certain implementations.

The infusion set adapter 30 comprises a valve device 34, 35 which is arranged in the liquid path between the cannula 33 and the infusion line 31. The valve device 34, 35 has in principle two functions. Firstly, it is intended to prevent liquid from flowing back from the infusion line 31 into the administering apparatus 1. Secondly, product is to be prevented from undesirably flowing out, for example due to differences in pressure. While backflow is to be prevented completely, the flow of product for the purpose of administering product is to be possible, but only beyond a certain minimum pressure in the product container, wherein a compromise has to be drawn between safety (preventing product from undesirably flowing out) and obstructing the actual administering process as little as possible. The infusion line 31 typically has a length of 30 to 120 cm, which then corresponds to about the distance between the administering apparatus 1 and the administering location on the body of the person using the device. Assuming an unfavorable scenario, the difference in height between the administering apparatus 1 and the administering location may be roughly one meter, thus establishing a column of liquid having a corresponding height, which corresponds to a hydrostatic pressure of about 0.1 bar. As already mentioned, the carpoule 2 comprises a carpoule plug 4 which is movably mounted in the carpoule 2. In order to deliver product from the carpoule 2, the carpoule plug 4 is pressed towards the septum 3, i.e. in the distal direction, by means of the piston rod 52 and the cap flange 53. The carpoule plug 4 is not retained by the cap flange 53, i.e. the connection between the cap flange 53 and the plug 4 cannot absorb any tensile forces. If the friction between the carpoule plug 4 and the carpoule wall is sufficiently small that the difference in pressure just described can cause the plug to be shifted, then the drug will undesirably leak out. The carpoule 2 has a typical inner diameter of about 9.25 mm; at a difference in pressure of 0.1 bar, a force of about 0.7 N can therefore act on the plug 4. EN ISO 11608-3:2000 specifies that the dynamic frictional force should not exceed 20 N and that the breakaway force of the carpoule plug 4 should not exceed 40 N. In practice, however, the values are significantly lower, in the range of about 10 N or less. Frictional forces which are as low as possible are desired, so that as little drive energy as possible is lost through frictional losses. Optimizing the frictional forces, however, increases the risk of undesirable leakage in accordance with the rough calculation employed above. The valve device 34, 35 takes account of this risk. In addition to the first function as a reflux valve, the valve device 34, 35 also functions as a threshold value valve. The valve is configured such that a typical (example) minimum pressure of about 0.3 bar in the product container has to be reached in order to open the valve and consequently enable the drug to be administered, wherein the minimum pressure can be tailored to a particular application. FIG. 4 shows the infusion set adapter 30 in an exploded representation. FIG. 6 shows the infusion set adapter 30 in a sectional representation, wherein the section is taken through the liquid path. The distal end of the cannula 33 feeds into a valve space 34. A valve membrane 35 is arranged in this valve space 34. On the right above the valve membrane 35, the valve space 34 feeds into the intersection 36a to the receptacle 36 for the infusion line 31. The infusion line 31, as well as the distal housing 30b of the infusion set adapter 30, are embodied in materials, in particular plastic, which can be adhered or welded to each other—such that a liquid-proof connection is created. Alternatively, the receptacle 36 can also be embodied as a Luer cone, wherein the infusion line 31 comprises a corresponding counter-piece. The valve space 34 is designed so as to be rotationally symmetrical, in particular round, relative to the longitudinal axis of the cannula 33. The valve membrane 35 also comprises a round base area. The valve membrane 35 is clamped between the proximal housing 30a and the distal housing 30b, wherein the centering cam 30c of the distal housing 30b presses a central region of the valve membrane 35 in the proximal direction. The periphery of the valve membrane 35 lies on a sealing edge 34a of the valve space 34. Due to the pressure built up by the centering cam 30c and the corresponding elastic forces in the membrane 35, the liquid path is closed by the valve membrane 35 along the line of contact between the valve membrane 35 and the sealing edge 34a. The valve membrane 35 is made of a flexible material, for example rubber or another elastomeric material. The outside of the valve membrane 35 comprises the centering aids 35a which are important for assembling the infusion set adapter 30, see FIG. 4 in this respect. For assembling, the valve membrane 35 is inserted into the distal end of the proximal housing 30a. The centering aids 35a, which in the form shown are formed as nubs 35a, enable the valve membrane 35 to be centrally positioned in the housing without consequently obstructing the transport of product through the infusion set adapter 30 or impairing the valve characteristics due to the contact between the nubs 35a and the wall of the infusion set adapter 30. As soon as the valve opens due to deformation of the valve membrane 35, the nubs 35a of the valve membrane 35 can no longer touch the wall of the infusion set adapter 30 and thus do not influence the valve characteristics. In order to minimize the volume of the valve space 34, the wall of the distal housing 30b on which the centering cam 30c is arranged is shaped so as to be convex towards the valve space 34.

If pressure is built up on the proximal side of the valve membrane 35 and exceeds a particular threshold value, then the periphery of the valve membrane 35 is deflected in the distal direction and the valve opens in order for product to flow through it in the distal direction. If the pressure falls below the threshold value or a pressure burden is established on the distal side of the valve membrane, then the valve closes itself off, forming a seal, wherein the threshold value corresponds to the minimum pressure mentioned further above and is about 0.3 bars of relative pressure difference in the example shown.

In order to reduce the danger of the valve membrane 35 sticking to the sealing edge 34a, the valve membrane 35 in one example does not completely close at pressures less than 0.3 bar. To this end, a small, defined leakage in the form of a micro-channel or micro-notch (not shown) is arranged on the sealing edge 34a, wherein the leakage is dimensioned to be sufficiently small that at the differences in pressure mentioned above, the greatest amount of product per unit time which can leak out is one which is harmless to the person using the device. Taking the example of insulin, this would mean a worst-case flow rate of 5 units of insulin per day. In this case, the leakage would exhibit a cross-sectional diameter of roughly 10 to 15 μm. Since half the diameter to the fourth power features in the Hagen-Poiseuille flow equation using which the flow rate is estimated, the greatest attention must be paid to the precise dimensioning of the leakage diameter. The defined leakage in the valve device 34, 35 has the advantage that, due to the defined leakage, minimal amounts of product can flow out even when the threshold value of the drive pressure has not yet been reached, which enables the valve device 34, 35 to be prevented from drying out completely. This example presupposes that the product to be administered is compatible with the micro-leakage. Suspensions may for example impair the functionality of the leakage.

The administering device can be programmed and controlled by the person using the device. To this end, the administering apparatus 1 comprises a touch display 20 and a function key 10, both of which are connected to the control module 80. The control module 80 can display a menu structure on the touch display 20. The person using the device can control the administering apparatus 1 or also for example retrieve and display the administering "history" via the touch-sensitive touch display 20, with the aid of a finger or suitable pointer and the support of the menu structure. The person using the device can also program the types of administering. The person using the device can for example store a basal rate profile in the apparatus 1, which then controls how product is administered, in a time-controlled way. It is also possible for boluses to be dispensed immediately or with a time delay. As an alternative or complement to controlling the administering device via the touch display 20, a simplified form of control via the function key 10 is possible. In one function, the function key 10 serves as an on/off key or as a standby key. In another function, the function key 10 serves as a programming and triggering key for so-called blind boluses, i.e., activating the administering device to dispense boluses without the administering device having to be controlled via the touch display 20. This is advantageous because the person using the device can wear the administering apparatus 1, hidden from other people, while programming and triggering blind boluses. The boluses can thus be discreetly programmed and triggered. In order to acknowledge inputs or accentuate alerts, the administering apparatus 1 also comprises a vibration device 82 and a buzzer or loudspeaker (not shown). When programming and administering blind boluses, the vibration device 82 in particular can discreetly provide the person using the device with feedback regarding the bolus amount set, namely with a particular number of vibration pulses, and that the bolus has been successfully administered.

Figure 7:
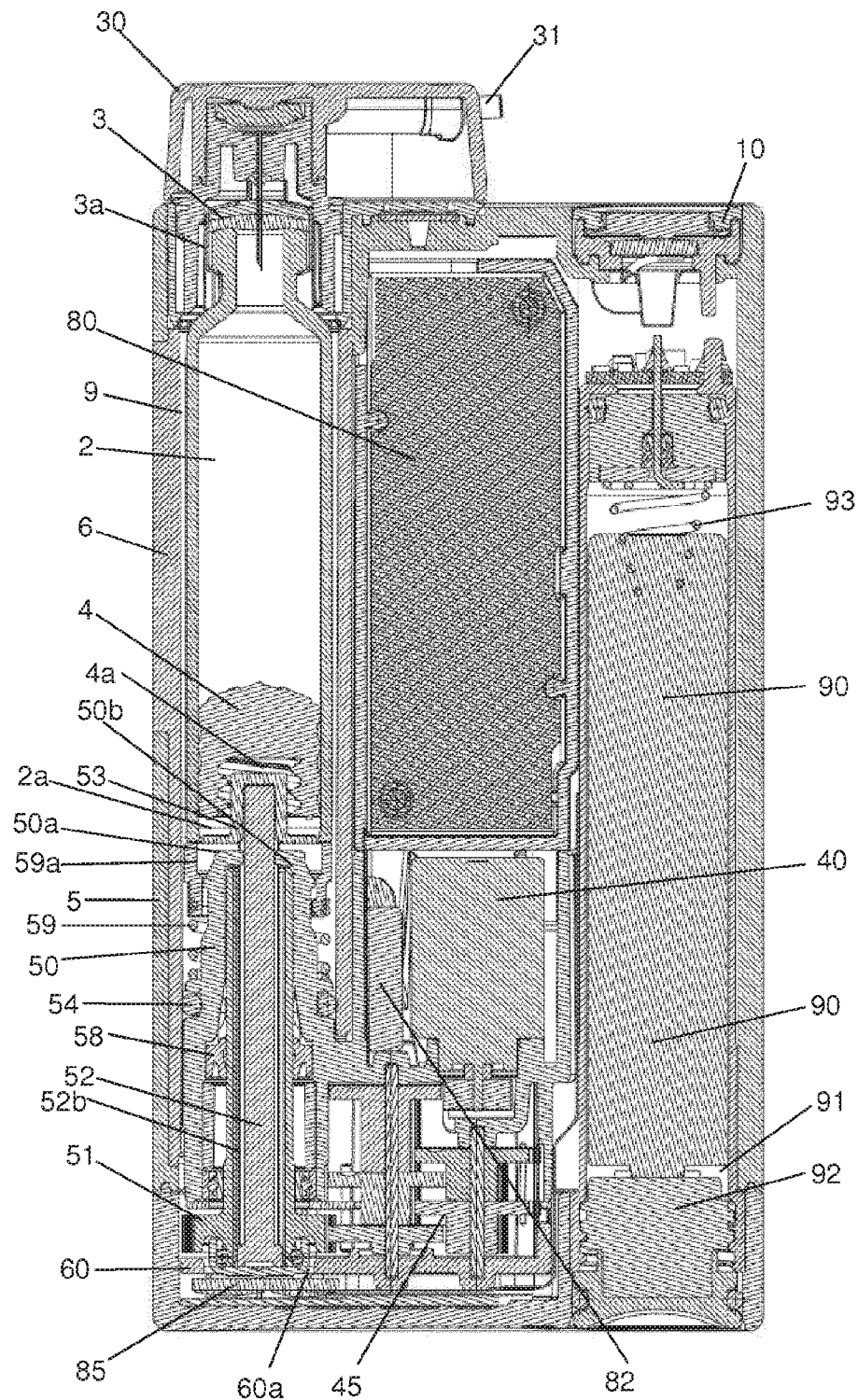
FIG. 7 illustrates a cross-sectional view of an infusion device according to certain implementations.

With respect to controlling the touch display 20 by means of a finger, it is also conceivable in one example for gestures using multiple fingers simultaneously to be recorded by the touch display 20. Such gestures are known from the literature as multi-touch gestures. FIG. 7 shows an example, wherein reference is made to the descriptions of FIGS. 2a and 3g. The example shown in FIG. 7 does not comprise the housing evacuator 8 (or venting), the membrane 8a, the evacuating protection 8b, the aperture 8c and has especially no housing opening 8d. The only way to connect the inside of the housing 5, in which the battery 80 and the drive mechanism 40, 45, 50, 51, 52, 53, 55 and 56 is arranged, to the outside of the infusion device by allowing the passage of air is through seal 54 and optionally also through seal 57 (see, e.g., FIG. 3g) and/or 58, which seal 54 is located between an element of the drive mechanism, such as for example the shown drive housing 50 being on the inner side of seal ring 54, and viewing window 6 or housing 5 being on the outside of seal ring 54. Seal 54 is made from a material allowing the passage of air and inhibiting the passage of liquids or water and is preferably in tight contact or bonded to the housing 5, 6 and to the drive housing 50 so that no unsealed opening is between the housing compartment and the carpoule compartment 9.

As mentioned above, seal or O-ring 54 can for example be made of Polytetrafluoroethylene (PTFE), microporous expanded PTFE (ePTFE), High-density polyethylene (HDPE), Polyethersulfon (PES), polydimethylsiloxane (PDMS), Polyetherester, Ultra-high-molecular-weight polyethylene (UHMW) polymers and can for example be Gore-Tex®, Polyphobe™ Porex®, Sympatex®, eVent® fabrics, Filtrone.

Figure 8:
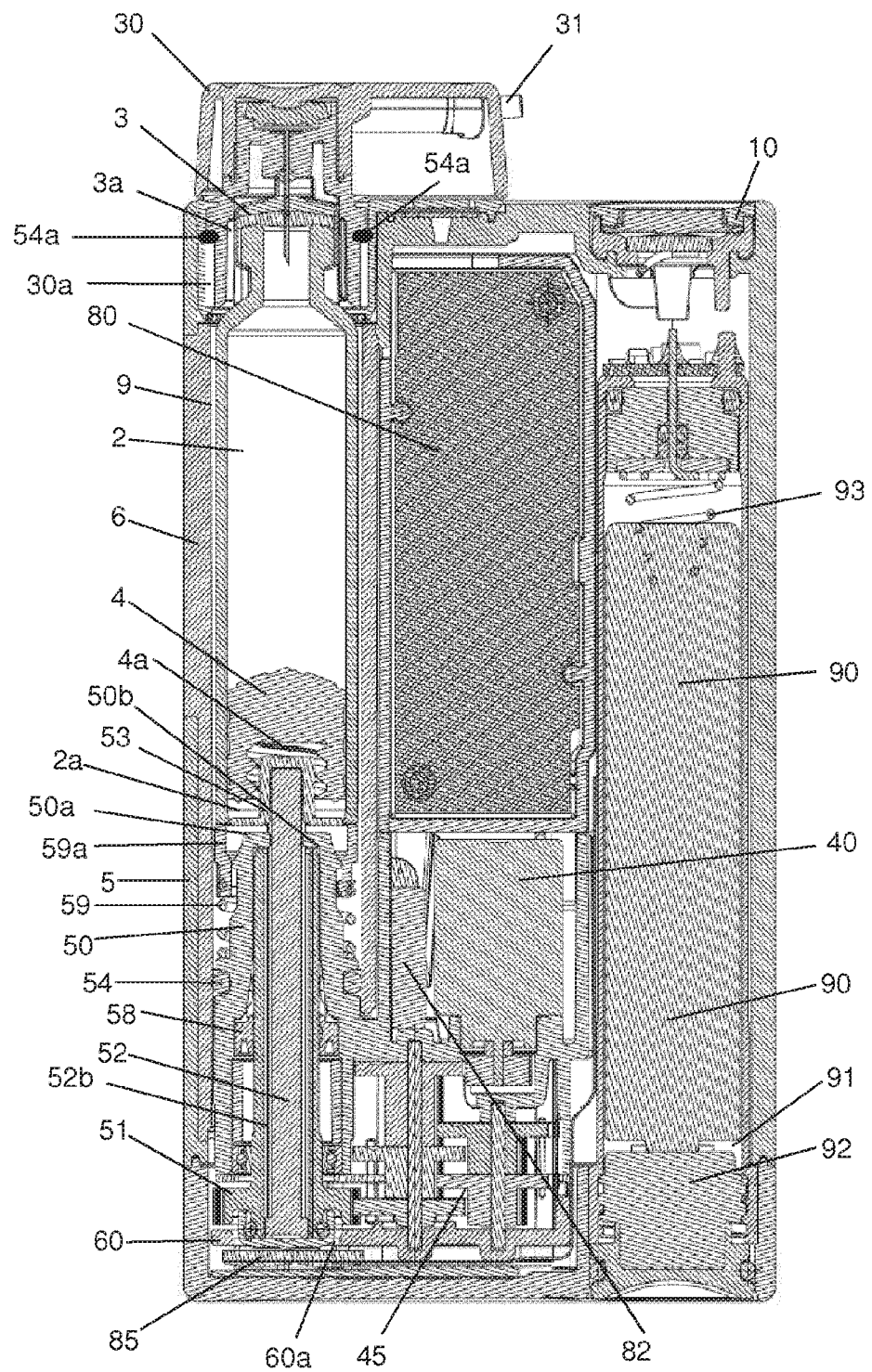
FIG. 8 illustrates a cross-sectional view of another infusion device according to certain implementations.

FIG. 8 shows a further example, wherein seal 54 can be made from a material allowing the passage of air and inhibiting the passage of liquids or water or can be a conventional seal. A further location for a seal 54a is shown on the upper or distal side of the housing 5. Seal 54a is attached on the inner side or side wall of the carpoule compartment 9 to be in contact with the housing 30a of the infusion set adapter 30 as mentioned above, when the infusion set adapter 30 is placed onto the infusion device.

Figure 9:
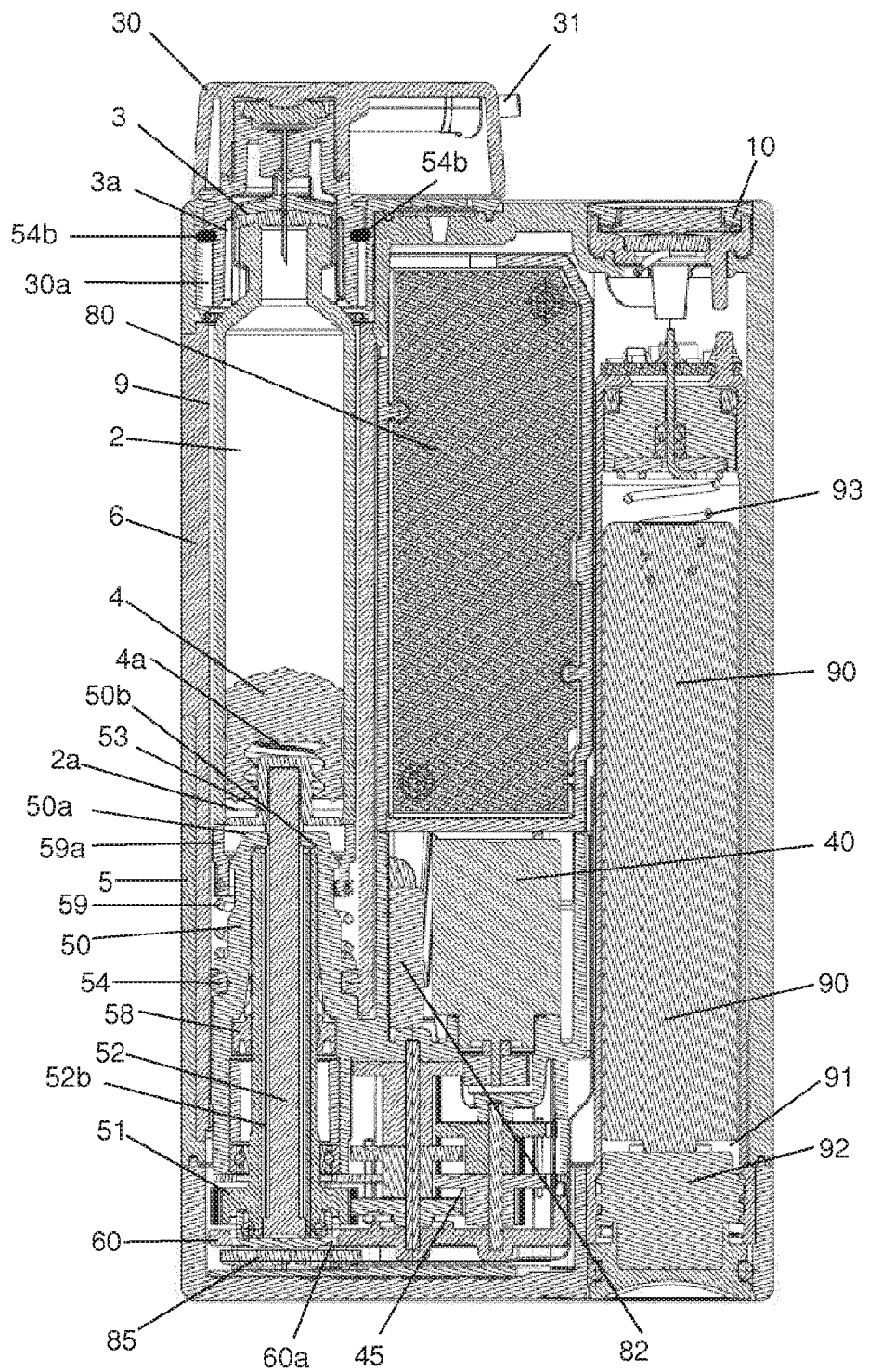
FIG. 9 illustrates a cross-sectional view of still another infusion device according to certain implementations.

FIG. 9 shows a further example, wherein seal 54b being made from a material allowing the passage of air and inhibiting the passage of liquids or water and being a seal ring is attached to the outside of the proximal housing 30a of the infusion set adapter 30 and is brought into a position to be in contact with the inner wall of the carpoule compartment 9 once the infusion set adapter 30 is placed onto the administering apparatus 1.

Figure 10:
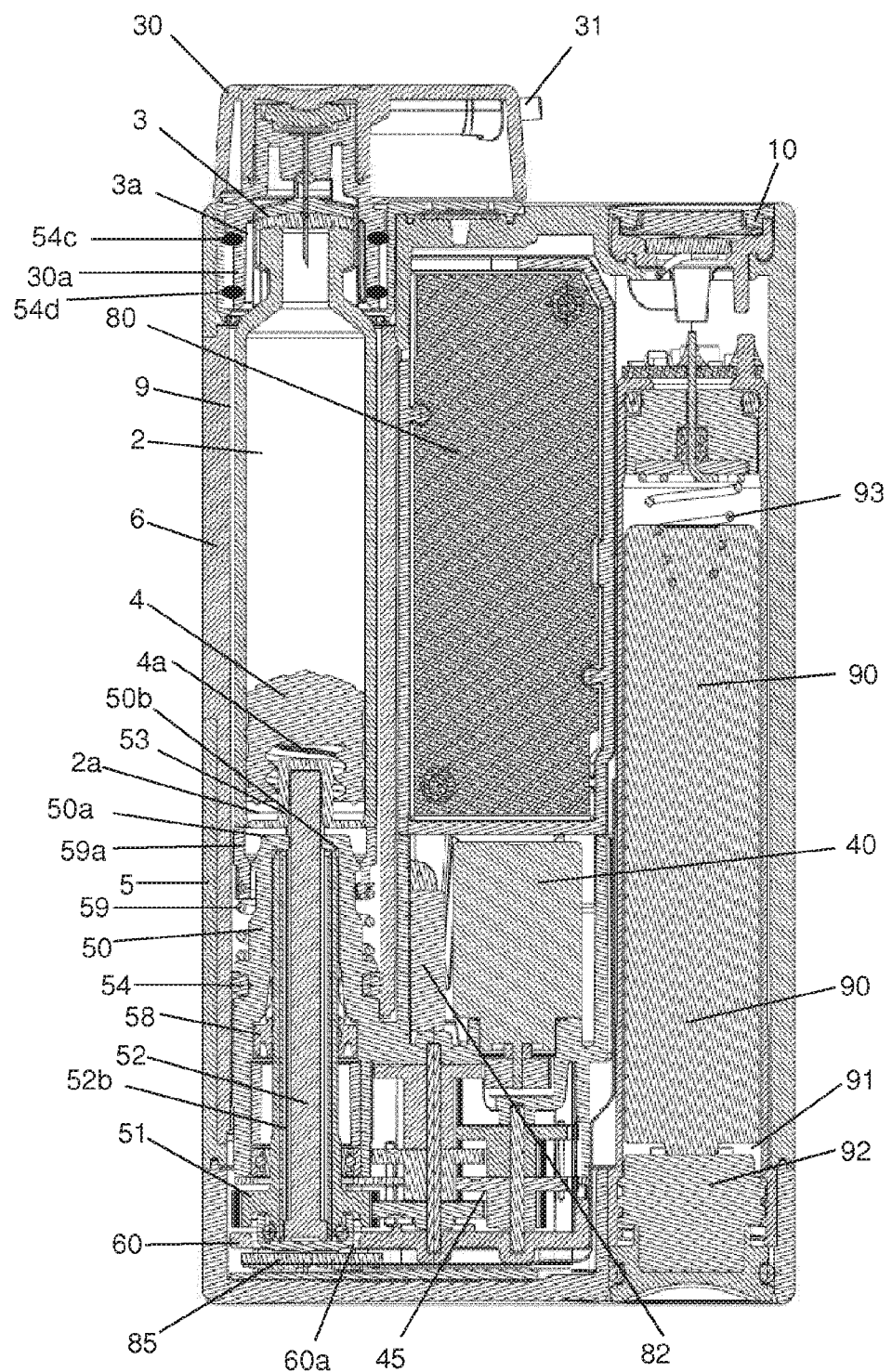
FIG. 10 illustrates a cross-sectional view of yet another infusion device according to certain implementations.

FIG. 10 shows a further example wherein two sealing elements 54c and 54d both being made from a material allowing the passage of air and inhibiting the passage of liquids or water and being sealing rings are attached to the outside or outer circumference of the proximal housing 30a of the infusion set adapter 30 to be in contact with the inside or inner wall of the carpoule compartment 9 when being placed thereon.

In a further example, an infusion set adapter 30 for an infusion set, comprising: a housing 30a, 30b; a liquid path which extends through the housing 30a, 30b and comprises a liquid inlet 33 and a liquid outlet 36; and a membrane valve 34, 35 which is arranged in the liquid path and comprises an inlet and an outlet, wherein the membrane valve 34, 35 comprises a valve space 34, which is limited by walls, and a valve membrane 35, and wherein a valve seating 34 onto which the valve membrane 35 can be placed is arranged in the valve space 34, characterized in that at least two centering aids 35a are arranged on the walls or the periphery of the valve membrane 35 and in particular simplify centrally positioning the valve membrane 35 on the valve seating 34a when assembling the infusion set adapter 30. The infusion set adapter 30 for an infusion set as described above, wherein the valve membrane 35 comprises the centering aids 35a at its periphery as radially aligned and nub-shaped centering aids 35a.

The infusion set adapter 30 for an infusion set as described above, wherein the housing 30a, 30b comprises a proximal housing 30a and a distal housing 30b, wherein the liquid outlet 36 is arranged on the distal housing 30b and the liquid inlet 33 is arranged on the proximal housing 30a.

The infusion set adapter 30 for an infusion set as described above, wherein the walls of the valve space 34 are formed by the proximal housing 30a and the distal housing 30b.

The infusion set adapter 30 for an infusion set as described above, wherein the valve membrane 35 is shaped as a circular disc and, when assembling the infusion set adapter 30, can be inserted into a space in the proximal housing 30a which is shaped complementarily with respect to the disc, wherein when the membrane 35 is not mechanically stressed, the centering aids 35a can touch a wall of the complementarily shaped space.

A device for administering a fluid product, comprising an administering apparatus 1 and an infusion set, wherein the infusion set can be detachably connected to the administering apparatus 1 by means of an infusion set adapter 30 as described above, such that a liquid path between the infusion set and the administering apparatus 1 is created.

A device for administering a fluid product, comprising an administering apparatus and an infusion set, wherein the infusion set can be detachably connected to the administering apparatus by means of an infusion set adapter, such that a liquid path between the infusion set and the administering apparatus is created. The infusion set adapter comprises a membrane valve, wherein the membrane valve comprises centering aids for simplifying the positioning of the membrane.

Figure 11:
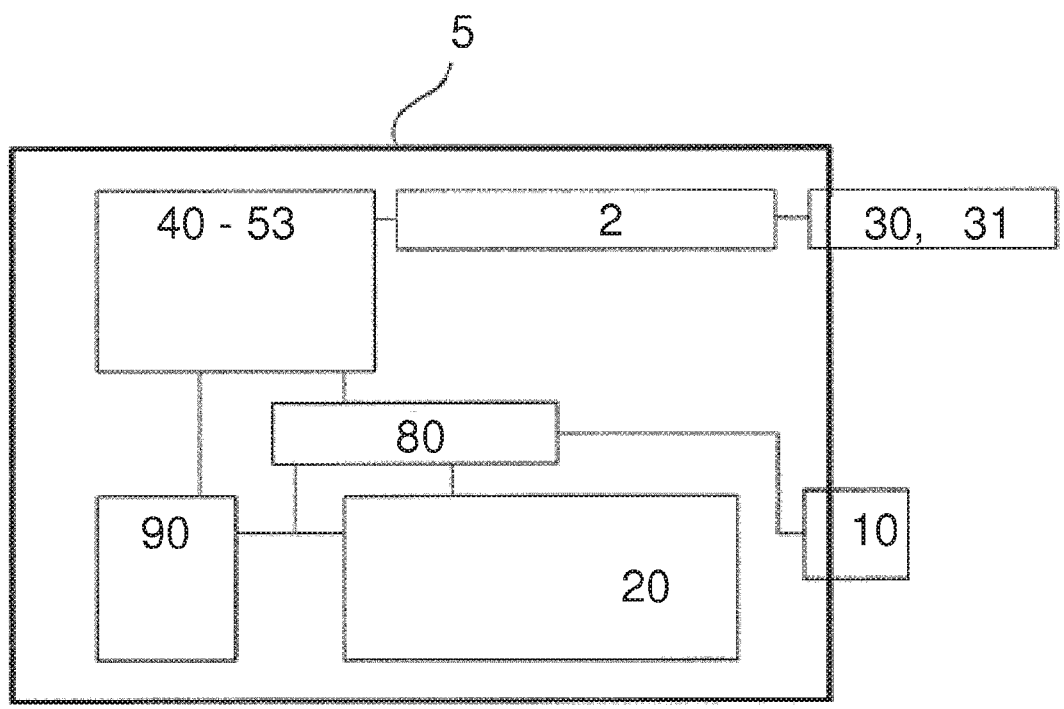
FIG. 11 is a schematic representation of an infusion system according to certain implementations.

FIG. 11 relates to a further aspect.

One common therapy for treating auto-immune diseases (for example, type 1 diabetes) involves near-continuously supplying a drug (for example, insulin) for the entire duration of the therapy, with the aid of a portable pump. In the case of diabetes, the pump therapy enables a (variable) basal rate of insulin to be continuously dispensed, as well as individual boluses which are employed in connection with mealtimes and for correcting excessively high glucose values in the patient's blood. By continuously dispensing the basal rate in accordance with a user-specific basal rate profile, a more uniform blood sugar level is achieved and the patient's organism is thus unburdened. Infusion systems are correspondingly known which consist of an infusion pump for insulin (insulin pump), a supply line to the body (infusion set) and, as applicable, a remote control. In general, the insulin pump is to be formed so as to be as compact as possible, so that it is not too bulky and is comfortable for the user to wear. The pump thus comprises a small pump housing which accommodates a battery, a motor including a gear system and control and communications electronics, and an ampoule which is connected to the infusion tube, forming a seal. The outside of the pump comprises operating keys and in most cases a display. This display, as well as the size and number of the operating keys, is limited by the structural shape which is to be realized. At the same time, operating them should be as simple and intuitive as possible, so that the users of the infusion system can perform the therapy themselves.

The conventional displays and keys which have been used up to now result in solutions involving confusing displays and/or complicated operating steps using various keys. Modern touch displays, such as are used in smartphones, make them simpler to operate and clearer, but can hardly be used in insulin pumps for reasons of price and space and power consumption. This approach has hitherto only been pursued in remote controls.

Moreover, the requirement to administer a bolus "blind" necessitates the use of keys.

In a further example an infusion pump is presented, and a method for controlling a user interface of such a system, which enable a large range of functions and a simple mode of operation, even when using miniaturized components. This object is solved by an administering apparatus, in particular a portable infusion pump comprising a touch-sensitive display and an additional operating element, characterized in that the operating element is a key.

The touch-sensitive display can be a touch display or touch screen.

The touch screen or touch display can comprise 128×256 pixels at most.

The administering apparatus can comprise precisely one single additional operating element. The precisely one or single additional operating element can be an electro-mechanical key (push-button).

The precisely one or single additional operating element can be an electromechanical key. The precisely one or single additional operating element can be a piezo-resistive key. The precisely one or single additional operating element can be an optical key.

A feedback device can be provided at or in the administering apparatus, which feedback device can generate a tactile, acoustic or optical feedback as a response to the additional operating element being operated. In one example, four concepts interact which are realized by the components mentioned: an operating concept comprising a touch display, i.e., a touch-sensitive display, and a single operating element, in particular a single mechanical key; an infusion set comprising an integrated pressure valve and a carpoule adapter; a drive concept comprising a deflection gear system and an integrated monitor; and a feed concept comprising a supporting power pack. Each of these concepts exhibits particular features in detail, which in their entirety result in a mode of operation which is substantially simplified as compared to conventional infusion pumps, but at the same time can be miniaturized.

The operating concept is characterized by: a display consisting of 128×256 pixels at most; a gesture recognition system, in particular a capacitive gesture recognition system, which recognizes taps and swiping movements made by an individual finger; and an individual and in particular mechanical key which on the one hand enables the touch display to be activated and on the other hand enables a bolus to be programmed without using the display.

During normal operation, the display is switched off. It is activated by a keystroke and displays a summary of the current status. A swiping movement switches to a menu display which consists of a row of symbols. The symbols/sub-menus can be moved in and out of the visible region by left and right swiping movements, and selected by tapping them. The submenus consist of functional displays or screens which show displaying and setting options depending on the function. A keystroke cancels an initiated input and returns to the next respectively higher level. The operating concept described here can be implemented in both landscape and portrait format. It is also possible to program a "blind" bolus using the key, which is in particular a mechanical key, thus circumventing the touch display, wherein a bolus is triggered without the need for eye contact or interaction with the display, for example while carrying the pump in one's trouser pocket or wearing it beneath one's clothing. To this end, the key is sequentially operated as follows:

A long keystroke, in order to activate the blind bolus function;

Short keystrokes, acknowledged by tactilely perceivable signals from the pump, in order to input the bolus amount in predefined incremental increases;

A pause, upon which the pump system acknowledges the programmed amount, via tactile signals;

A long tactile signal by the pump, asking blind bolus confirmation;

A confirmation of the blind bolus by a long keystroke within a certain time;

Delivery commences;

Any keystroke during delivery cancels the current delivery.

This series of keystrokes realizes a very simple mode of operation, with a very high level of security against unintentionally triggering the delivery of a bolus.

In accordance with the examples described above, the infusion set consists of the following elements: a carpoule connector; a pressure valve; and a transition line into the patient's body. The result of integrating these elements is that the infusion system is simpler and more secure to operate. In particular, it enables incompletely filled carpoules to be used, a warning to be issued when the system is put into operation with no carpoule, and the operation of the system to be monitored during delivery.

In accordance with the examples described above, the drive concept comprising a deflection gear system and an integrated monitor consists of: a drive comprising a rotary position monitor (encoder); a force transmission, arranged parallel thereto, onto the carpoule stopper; and a deflection gear system which deflects the rotational movement of the drive and at the same time converts it into a linear thrust, wherein the deflection gear system is integrated into the pump housing in such a way that the force exerted on the carpoule stopper can be measured using a force sensor. This arrangement enables a shorter and therefore more user-friendly structural shape of the pump system.

The power supply concept comprising a supporting power pack consists of a primary and a secondary energy source and a controller. The primary energy source is exchangeable and chosen such that it is as simple as possible for the user to replace (standard size AA, AAA or AAAA battery, operated without any special tools). The secondary energy source, for example a lithium polymer battery, is fixedly installed, rechargeable and fed from the primary cell. The charging of the secondary cell by the primary cell can be in a normal mode (continuous charging) or in a fast, turbo charging mode where the secondary cell is charged for example in less than 1 hour, preferably less than 30 minutes, e.g., 10 minutes or less. The power supply arrangement including a secondary source ensures on the one hand that the primary cell can be exchanged without interrupting the therapy, and on the other hand enables a warning to still be issued if the primary cell fails or an internal line is cut. A first alarm can be triggered if the primary cell voltage drops below a level where normal operation of the infusion apparatus is guaranteed for a restricted but still relatively long period, for example 1 or 2 days. A second alarm is triggered when the voltage drops below a level where immediate replacement of the primary battery is required because otherwise a dose delivery would be jeopardized. Additionally an automatic battery recognition system may be included which automatically identifies what type of rechargeable (e.g. Lithium Ion, Nickel Metal Hydride, Nickel Cadmium) or non-rechargeable (e.g. Alkaline) battery is inserted by the user. Each type of battery has a specific discharge profile and thus calls for different alarm conditions for a safe operation of the device. The arrangement described thus enables a very simple mode of operation and at the same time the highest level of operational security.

The components of the infusion system shown in FIG. 11 are a housing 5, a mechanical drive 40-53, an energy source 90, a drug reservoir 2, a transition line to the patient's body (infusion set 30, 31), a touch-sensitive display or touch display 20, a key 10 and a controller 80.

Figure 12:
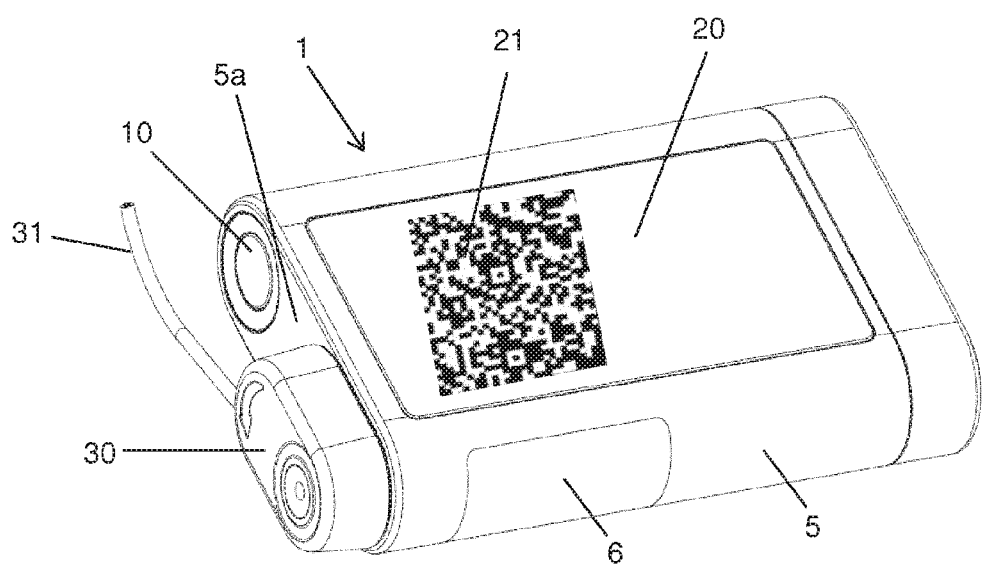
FIG. 12 is an example of an infusion device according to certain implementations.

FIG. 12 shows a further aspect being an infusion pump having a display 20 being able to display a code, such as a data matrix code 21. This data matrix code can be Data Matrix ECC 200 (a well-known error checking and correction algorithm). The data shown or encoded by the data matrix 21 can comprise or include data concerning the infusion pump itself and/or data concerning the functioning or working of the infusion pump, such as the infusion pump history. Data included in the infusion pump history can for example be data indicating what amount of medication was delivered over time, such as data concerning the basal rate and data concerning one or more boluses delivered by the infusion pump.

This infusion device can be combined with the above described aspects or can be independent thereof. The displayed code can be a bar code instead of the mentioned matrix code and can be any readable code which is able to display information or to transfer information from inside the infusion device, such as information from a memory or processor 80 inside the infusion device to the display 20. The encoded information displayed on the display device can be read with an appropriate reading device having a camera, such as a mobile telephone, a camera connected to a computer or any other kind of camera connected to an electronic device. Such a display can also be provided at a medical measuring device, such as at a blood glucose measuring device. In this case the data provided by the blood glucose measuring device and the data provided by the infusion pump can both be read by a camera and can be associated with each other using an electronic device. The data graphically displayed on the display 20 can provide a serial communication where a sequence of information, for example a sequence of matrix codes or bar codes or pixels, e.g. a single blinking pixel, can be displayed. Each single code of the sequence can be displayed for a predetermined amount of time, such as for one second, where after the next code of the sequence is displayed until the last code required to transmit or display the desired information is reached. This displayed sequence of codes can be scanned by the mentioned camera connected to an electronic device which is able to extract the information from the displayed sequence of codes.

In case a single pixel is used, the display and the viewing or receiving device act as optocouplers.

It is possible to provide a parallel communication on the display, which parallel communication can be provided using a clock signal and several data pixels or picture elements or picture areas. The display can for example be divided into a predetermined number of fields, such as for example into four, nine or 16 fields. Each field can then transmit a specific type of information by displaying a single picture or single data code or by providing a serial communication as described above, such as by providing a sequence of graphical codes. To provide a scannable graphical code the infusion pump includes a graphical code generator, which can be included or part of the electronic control module 80 or can be a separate device, which is provided from an internal electronic device of the infusion pump, such as a processor which can be connected to a memory device, with the information to be transformed into the graphical code, matrix code or bar code by the code generator. The input data can be configuration data of the infusion pump, device data, system state data and infusion or delivery history data.

The code generator is connected to a display 20 for displaying the code, which display can be a transmissive display, such as a backlit LCD display, or can be a regular LCD display or can be a reflective display, such as an electronic paper or can be an OLED or a AMOLED display.

The graphical code can be a bar code or a data matrix code 21 and can in general be any kind of code which is able to transport or transfer information once the code is displayed.

The scanning device can include electronics to obtain the information included in the scanned graphical code. According to an example, an appropriate configured scanning device, such as a mobile phone or computer, can include a browser able to view a given web page associated with an Uniform Resource Locator (URL) included in the displayed graphical code and can display the contents of the thus specified web page. Alternatively, an application or software application on a mobile phone can scan and identify the graphical code and display its contents on the display of the phone.

The information included in the graphical code can specify a particular alarm of the infusion pump or indicate malfunction and optionally data associated with the malfunction, such as data specifying the pressure detected by an internal pressure sensor of the infusion pump in case an occlusion is detected.

An infusion pump system can comprise a display 20 for rendering a scannable graphical code, such as a one-dimensional or two-dimensional code, for example a bar code or a matrix code.

The display 20 is preferably integrated within the infusion pump.

The infusion pump preferably includes a graphical code generator for generating a scannable graphical code based on input information.

The input information can be selected from a group consisting of: configuration data, device data, system state data, device history data, infusion history data, device alarm data and malfunction data. The graphical code data generated by the code generator can be a static data or can be a serial communication data consisting of a sequence of separate data units, such as a sequence of separate graphical data or can be a parallel communication data providing in parallel graphical code data on specified fields of the display device 20 optionally using a clock signal.

A method for displaying a graphical code on a display 20 of an infusion system comprises the steps: obtaining data from an electronic device inside the infusion pump; transforming this data into a graphical code; and displaying this graphical code on a display 20 of the infusion pump.

The step of displaying can be a static display, for example the display of a single graphical code for a predetermined amount of time or until a specific event, such as pressing a button 10 of the infusion pump.

Alternatively, the step of displaying includes the display of a sequence of graphical codes consisting of separate individual graphical codes. This sequence can be displayed using a predefined clock signal to display each of a series of graphical displays in sequence, wherein each graphical code is displayed for a predetermined amount of time. Alternatively, the sequence can be triggered by an external event, such as by pressing a button 10 on the infusion pump, so that a user can for example flip through the code sequence.

As described previously, the infusion apparatus, the functioning of the device is monitored using other sensors that can measure temperature, humidity, mechanical impact or pressure, this to ensure that the housing of the device is intact and to protect the drive mechanism and control unit from environmental influences. Furthermore the viewing window of the housing may protect the medication in the infusion apparatus. These functionalities are described in more detail below. Measuring the temperature inside the infusion apparatus is a safety feature that prevents deterioration of the medication and/or mechanical damage to the infusion apparatus. The temperature sensor (for example a Sensirion STS21) is included inside the infusion apparatus and measures the temperature at one or more of the following locations: The temperature in the drive housing (50), in the electromotor or the motor compartment (identical to the location 82 for the vibrational alarm), in the battery compartment (91), in the carpoule compartment 9, on the surface of the carpoule (2) itself, the adapter (30) for the infusion set or the tubing (31) used for transporting the medication from the infusion device to the injection site. The sensor measures the temperature and the signal is sent to an electronic module. The measured temperature is compared with a defined alarm value and the electronic module triggers an alarm if the temperature exceeds the alarm value. The alarm is a tactile, audible or visual signal that is easily notified to the user of the device. Furthermore, the alarm can be sent by wireless communication to another device such as a remote control for the infusion pump or a blood glucose measuring unit or to a cellular phone or a personal computer or any other network device or software implemented application. The alarm is logged in a history file of the infusion device or any of the devices receiving the signal from the infusion device.

In one example, the humidity sensor is included in the device to prevent any damage on the electronic parts from liquids that enter the device. Such a humidity sensor (for example a Sensirion SHT 10) is included in any one of the compartments mentioned above for the temperature sensor. The humidity sensor can be included in the drive housing (50), in the electromotor or the motor compartment, in the battery compartment (91), in the carpoule compartment 9, on the surface of the carpoule (2) itself, in the adapter (30) for the infusion set or the tubing (31). The sensor measures the humidity level and the control unit compares the measured value with an alarm level and triggers the alarm if the humidity exceeds the alarm level. The alarm triggered is a tactile, audible or visual alarm and is notified on the display of the device or sent to a receiver as described above for the temperature sensor system.

The pressure sensor functionality is described in more detail below. During delivery of the dose, the advancing sleeve 51 is rotated by the motor driven gearing system. The advancing sleeve 51 has a threading on the inside matching the outside threading of the piston rod 52. After reset of the device, the piston rod is in its most proximal position as is graphically presented in FIG. 3c. A carpoule is inserted in carpoule compartment 9 and the infusion set adapter 30 is attached to the housing. During delivery of a medicament, e.g., insulin, the piston rod 52 is advanced in the distal direction. In the most distal position, all medication is expelled from the carpoule and this situation is presented in FIG. 3f, before reset of the piston rod which is needed to insert a full carpoule. Due to the advancement of the piston rod in the distal direction, the volume V2 inside the drive housing 54 has increased compared to the situation after reset (FIG. 3c) having volume V1. These volume changes inside the housing result in corresponding pressures P1 and P2 inside the housing since the housing is sealed from the carpoule compartment 9 by the drive house sealing 54. A pressure sensor is located inside the drive housing or any other part of the housing that is not air tight sealed from the drive housing. For example, the pressure sensor can be located next to the force sensor 85 or even be combined with the force sensor. The pressure sensor transmits the pressure profile during dose delivery and reset to the electronic control unit 80 where the pressure profile is stored and, if needed, compared to a log file of the previous pressure profile or a predefined pressure profile loaded into the control unit during assembly of the infusion apparatus.

In the case of a watertight, non-air permeable housing, the pressure profile during reset and delivery cycles is constant with a highest pressure P1 after reset and a lowest pressure P2 after emptying a carpoule or before reset of the piston rod. If the housing or housing parts are cracked, the volume changes from V1 to V2 will not lead to a change of the pressure and a constant pressure value equal to the ambient pressure is recorded.

For an infusion device having a ventilating or evacuating device 8 (FIG. 2a) with membrane 8a allowing passage of gases but blocking liquids, the pressure sensor will normally record the ambient pressure and this pressure will be stored in the control unit. In case the ventilating or evacuating device 8 gets blocked or the membrane 8a gets contaminated, the volume changes from V1 to V2 due to the movement of the piston rod result in sudden pressure variations deviating from a relatively constant ambient pressure and these pressure variations are sent to the control unit which can trigger an alarm indicating that the ventilating or evacuating device 8 is blocked. The integrity and functionality of the infusion apparatus after a mechanical impact can also be monitored by integration of an acceleration sensor in the apparatus. During the impact, the sensor sends a signal to the control unit and the control unit triggers an alarm if the signal is above a safety limit indicating by visual, audible or tactile means an impact to the user of the device. A message is communicated to the user indicating that he should check the apparatus and/or send the infusion device to the manufacturer for a control check.

The values measured by the pressure, acceleration, temperature or humidity sensor are stored in the control unit versus time. Mathematical algorithms can be applied to the recorded data to smoothen the data such as integration or derivatives versus time, with or without Fourier transformation, calculation of averages or moving averages but also other algorithms can be applied. For example the acceleration versus time recoding can identify and differentiate between the normal walking, running or, in particular, the occurrence of a seizure due to over/under dosing of the medication. The measured values can also be used not versus time but versus each other, for example the measured pressure versus the temperature the humidity versus the pressure.

The recorded data values, with or without data processing using mathematical algorithms are compared with pre-defined threshold values or slopes or compared with threshold values calculated based on the recorded data in combination with predefined values.

The protection of the medication from UV/light exposure is described below. The viewing window (6) of the infusion apparatus that is in the light path of the medication, is made from a transparent plastic material such as Polyethyleneterephthalate (PET), Polystyrene (PS), Polycarbonate (PC), Cycloolefinic copolymer (COC), Polymethylmethacrylate (PMMA), Polyester or Copolyester (for example Tritan MX 731) or any other transparent polymeric material. To improve the protection for the medication against ultra violet radiation, UV absorbers can be embedded in the plastic material of the viewing window (6) during the extrusion process. Typical examples of such UV absorbers are Neo Heliopan AP or Tinosorb S or Lowilite absorbers. To improve the absorbing properties also in the visible wavelength range and to introduce the reversible photochromic effects, special compounds need to be added to the plastic material of the viewing window. Examples of such photochromic molecules are spiropyrans, spirooxazines, diarylethylene, azobenzenes, silverhalides or zinchalides. The photochromic molecules are embedded in the viewing window material and therewith provide the projection against UV/Visible light radiation when needed, e.g. during exposure to sunlight whereas the visibility of the carpoule and plug behind the viewing window is not impaired in a darkened environment. In another embodiment, the photochromic molecules are added to a coating that is applied onto the surface of the viewing window. The coating is solvent based or powder coating based with polyurethanes, polyesters, acrylates, styrenes, polycarbonate, PVC or the like as a carrier material.

In yet another example, the photo chromic molecules are added to and embedded in the labeling material (for example a transparent polyester film) that is used as an adhesive tape for the viewing window. The adhesive label can be applied onto the outside surface of the viewing window (6) therewith providing an extra scratch resistance or onto the inside surface of the viewing window (6). The photochromic entities are applied as a coating on the label as an alternative to embedding the molecules in the bulk of the labeling material. The adhesive label can also be glued directly onto the carpoule (2) or both onto the carpoule (2) and the viewing window (6). In another application, the UV protection based on photochromic additives described above is used for the infusion set between the administering apparatus (1) and the patient, more specifically to the infusion set adapter (30) or the infusion line (31).

The patient monitoring module comprises an acceleration sensor, a positioning sensor the electronic control unit (80) a wireless communication unit for sending data to an external receiver. The positioning sensor can be a GPS sensor for position identification on a global scale or a sensor using the GSM network for position identification on a regional level or a sensor that identifies the location using a local area network system (WLAN). The wireless communication unit comprises any electronic component able to send the information received from the control unit to an external receiver, examples are a GSM network unit or a WLAN receiver which is integrated in a personal computer, laptop or mobile phone. Upon a stroke, e.g., caused by hyper- or hypoglycemia, a collapse of the patient is recorded by the acceleration sensor and the sensor sends a signal to the control unit. The control unit (80) compares the value of the acceleration sensor with a predefined; if necessary patient specific, threshold value and triggers an alarm if the measured value exceeds the limit. The recorded values can be subjected to the mathematical algorithms described above. The alarm is sent to a receiver using the wireless communication unit together with specific data from the patient. Optionally also the file history log with the patient's medication history is sent by the control unit to the external receiver. The alarm is received by the external receiver which can act accordingly to prevent any further damage to the patient.

What is claimed is:

1. An infusion apparatus for the administration of a medication from a reservoir with a plug moveable along a central axis in a distal direction for ejection, the apparatus comprising:
    a housing;
    a drive device comprising an advancing sleeve and a piston rod, the piston rod configured for advancing the plug in the reservoir in the distal direction, the advancing sleeve configured for limited axial movement relative to the housing and being rotatable, wherein rotation of the advancing sleeve causes an ejection movement or a resetting movement of the piston rod;
    a force sensor arranged along the central axis between the housing and a proximal end of the drive device; and
    a closure cap axially arranged between the force sensor and the advancing sleeve such that the force sensor bears axial forces exerted by the ejection movement,
    wherein the piston rod moves the closure cap away from the advancing sleeve against the bias of a restoring force such that the force sensor bears axial forces exerted by the resetting movement.

2. The infusion apparatus according to claim 1, wherein a seal exerts the restoring force on the closure cap.

3. The infusion apparatus according to claim 2, wherein the seal is one or more of an elastomeric part or a spring.

4. The infusion apparatus according to claim 3, wherein the seal operatively couples the closure cap and the advancing sleeve.

5. The infusion apparatus according to claim 4, wherein the seal comprises an O-ring arranged in a groove formed on one or more of the closure cap or the advancing sleeve.

6. The infusion apparatus according to claim 2, wherein the seal is one or more of a magnetic or an electromagnetic arrangement.

7. The infusion apparatus according to claim 1, wherein:
    the closure cap comprises a protrusion and a protruding ring,
    the force sensor comprises a cantilever beam coupled to a base plate,
    the axial forces are measured by deflection of the cantilever beam versus the base plate, and are transmitted from the drive device to the cantilever beam via the protrusion, and
    a maximum deflection of the cantilever beam is limited by the protruding ring.

8. The infusion apparatus according to claim 7, wherein the protrusion and the protruding ring protrude from the closure cap.

9. The infusion apparatus according to claim 8, wherein a ratio of protrusion distances of the protrusion and protruding ring is above unity.

10. The infusion apparatus according to claim 7, wherein the maximum deflection of the cantilever beam is limited by the protruding ring touching the base plate of the force sensor.

11. An infusion apparatus for the administration of a medication from a reservoir with a plug moveable along a central axis in a distal direction for ejection, the apparatus comprising:
a housing;
a drive device comprising a first conveying member and a second conveying member, the second conveying member configured for advancing the plug in the reservoir in the distal direction, the first conveying member configured for limited axial movement relative to the housing and being rotatable, wherein rotation of the first conveying member causes an ejection movement or a resetting movement of the second conveying member;
a force sensor arranged along the central axis between the housing and a proximal end of the drive device; and
a transfer member axially arranged between the force sensor and the first conveying member such that the force sensor bears axial forces exerted by the ejection movement,
wherein the second conveying member moves the transfer member away from the first conveying member against the bias of a restoring force such that the force sensor bears axial forces exerted by the resetting movement.

12. The infusion apparatus according to claim 11, wherein a resilient member exerts the restoring force on the transfer member.

13. The infusion apparatus according to claim 12, wherein the resilient member is one or more of an elastomeric part or a spring.

14. The infusion apparatus according to claim 13, wherein the resilient member operatively couples the transfer member and the first conveying member.

15. The infusion apparatus according to claim 14, wherein the resilient member comprises an O-ring arranged in a groove formed on one or more of the transfer member or the first conveying member.

16. The infusion apparatus according to claim 12, wherein the resilient member is one or more of a magnetic or an electromagnetic arrangement.

17. The infusion apparatus according to claim 11, wherein:
the transfer member comprises a force transmitting member and a restricting member,
the force sensor comprises a cantilever beam coupled to a base plate,
the axial forces are measured by deflection of the cantilever beam versus the base plate, and are transmitted from the drive device to the cantilever beam via the force transmitting member, and
a maximum deflection of the cantilever beam is limited by the restricting member.

18. The infusion apparatus according to claim 17, wherein the force transmitting member and the restricting member protrude from the transfer member.

19. The infusion apparatus according to claim 18, wherein a ratio of protrusion distances of the force transmitting member and restricting member is above unity.

20. The infusion apparatus according to claim 17, wherein the maximum deflection of the cantilever beam is limited by the restricting member touching the base plate of the force sensor.

* * * * *